United States Patent
Levin et al.

(10) Patent No.: US 9,095,578 B2
(45) Date of Patent: Aug. 4, 2015

(54) ADENYLYL CYCLASES AS NOVEL TARGETS FOR THE TREATMENT OF INFECTION BY EUKARYOTIC PATHOGENS

(75) Inventors: Lonny Levin, New York, NY (US); Jochen Buck, Old Greenwich, CT (US); Leo Brizuela, Hamilton, MA (US); Michael Pinnisi, Ithaca, NY (US)

(73) Assignee: CORNELL RESEARCH FOUNDATION, INC., Ithaca, NY (US)

( * ) Notice: Subject to any disclaimer, the term of this patent is extended or adjusted under 35 U.S.C. 154(b) by 883 days.

(21) Appl. No.: 12/523,019

(22) PCT Filed: Jan. 11, 2008

(86) PCT No.: PCT/US2008/000447
§ 371 (c)(1),
(2), (4) Date: Nov. 9, 2009

(87) PCT Pub. No.: WO2008/088771
PCT Pub. Date: Jul. 24, 2008

(65) Prior Publication Data
US 2010/0063099 A1    Mar. 11, 2010

Related U.S. Application Data

(60) Provisional application No. 60/880,089, filed on Jan. 12, 2007.

(51) Int. Cl.
*A61K 31/4409* (2006.01)
*A61K 31/4184* (2006.01)
*A61K 31/045* (2006.01)
*A61K 31/4406* (2006.01)

(52) U.S. Cl.
CPC ........... *A61K 31/4184* (2013.01); *A61K 31/045* (2013.01); *A61K 31/4406* (2013.01)

(58) Field of Classification Search
CPC .................... A61K 31/4409; A61K 31/4184
USPC .................................................. 514/338, 395
See application file for complete search history.

(56) References Cited

U.S. PATENT DOCUMENTS

| | | | |
|---|---|---|---|
| 4,061,746 A | 12/1977 | Blohm | |
| 4,724,223 A | 2/1988 | Ditchek | |
| 5,602,110 A | 2/1997 | Drumm et al. | |
| 6,132,957 A | 10/2000 | Johnson et al. | |
| 6,309,648 B1 | 10/2001 | Betsou et al. | |
| 6,544,768 B1 | 4/2003 | Buck et al. | |
| 6,994,854 B1 | 2/2006 | Betsou et al. | |
| 7,438,909 B2 | 10/2008 | Morrow et al. | |
| 7,442,373 B2 | 10/2008 | Morrow et al. | |
| 7,462,472 B2 | 12/2008 | Tang et al. | |
| 7,786,139 B2 | 8/2010 | Bergmann et al. | |
| 7,906,123 B1 | 3/2011 | Leclerc et al. | |
| 7,947,268 B2 | 5/2011 | Baillie | |
| 2001/0041333 A1 | 11/2001 | Short et al. | |
| 2002/0032228 A1 | 3/2002 | Peterson et al. | |
| 2002/0169140 A1 | 11/2002 | Prendergast | |
| 2002/0188016 A9 | 12/2002 | Peterson et al. | |
| 2002/0197272 A1 | 12/2002 | Galloway et al. | |
| 2004/0006122 A1 | 1/2004 | Fensome et al. | |
| 2004/0009927 A1 | 1/2004 | Romeo et al. | |
| 2004/0180829 A1 | 9/2004 | Bassler et al. | |
| 2005/0271679 A1 | 12/2005 | Dadaglio et al. | |
| 2005/0287149 A1 | 12/2005 | Keler et al. | |
| 2006/0035909 A1 | 2/2006 | Fuksova et al. | |
| 2006/0099169 A1 | 5/2006 | Charmot et al. | |
| 2006/0159697 A1 | 7/2006 | Leclerc et al. | |
| 2006/0258842 A1 | 11/2006 | Groen et al. | |
| 2007/0059272 A1 | 3/2007 | Alverdy | |
| 2008/0063647 A1 | 3/2008 | Morrow et al. | |
| 2008/0124746 A1 | 5/2008 | Tang et al. | |
| 2009/0093519 A1 | 4/2009 | Schein et al. | |
| 2009/0234011 A1 | 9/2009 | Goldstein | |
| 2010/0035867 A1 | 2/2010 | Guerrant et al. | |
| 2011/0065782 A1 | 3/2011 | Malliavin et al. | |

FOREIGN PATENT DOCUMENTS

WO    01/85773 A2    11/2001
WO    2005/070419 A1    8/2005

OTHER PUBLICATIONS

Nguyen Huu Dinh, Hoang Thi Hue, Synthesis and Structure of some Derivatives of (benzothiazol-2-ylthio)acetylhydrazine, Journal of Chemistry, vol. 44 (4), p. 524-529, 2006.*
Patani et al. Chem. Rev., 1996, vol. 96, pp. 3147-3176.*
Cereto, F. et al., "Role of immunosuppression in the development of quinolone-resistant *Escherichia coli* spontaneous bacterial peritonitis and in the mortality of *E. coli* spontaneous bacterial peritonitis", Ailment Pharmacol Ther (2003), vol. 17, pp. 695-701.

(Continued)

*Primary Examiner* — Kendra D Carter
*Assistant Examiner* — Jason A Deck
(74) *Attorney, Agent, or Firm* — Kenyon & Kenyon LLP

(57) ABSTRACT

The present invention relates to a method of preventing or treating a disease caused by infection by a eukaryotic pathogen, wherein the method comprises administering an effective amount of a modulator of a eukaryotic pathogen's adenylyl cyclase. The invention also provides pharmaceutical compositions useful for preventing or treating a disease, with the compositions containing a therapeutically effective amount of a modulator of a eukaryotic pathogen's adenylyl cyclase. The invention also provides screening methods for identifying selective modulators of a eukaryotic pathogen's adenylyl cyclase that do not substantially modulate an adenylyl cyclase of the subject. The invention also provides methods for culturing eukaryotic pathogens and methods for inducing the pathogenic state in vitro.

27 Claims, 2 Drawing Sheets

(56) References Cited

OTHER PUBLICATIONS

Desai, K.G. et al., "Green route for the heterocyclization of 2-mercaptobenzimidazole into beta-lactum segment derivatives containing -CONH- bridge with benzimidazole: Screening in vitro antimicrobial activity with various microorganisms", Bioorganic & Medicinal Chemistry (2006), vol. 14, pp. 8271-8279.

Editorial "Cyanobacteria and human health", J. of Medical Microbiology (1992), vol. 36, pp. 301-302.

Gentile, F., et al., "*Bordetella pertussis* adenylate cyclase: preparation into host cells", European Journal of Biochemistry, (1988), vol. 175, pp. 447-453.

Gregg, J.P. et al., "Disease Cluster Found at Lake Research Seek Link Between Mascoma ALS, Algae", ALS Forums (Jun. 10, 2009), pp. 1-15.

Guo, Q. et al., "Strutural basis for the interaction of *Bordetella pertussis* adenylyl cyclase toxin with calmodulin" The EMBO Journal (2005), vol. 24, pp. 3190-3201.

Jones, A.M. et al., "Identification of airborne dissemination of epidemic multiresistant strains of *Pseudomonas aeruginosa* at a CF Centre during a cross infection outbreak", Thorax (2003(, vol. 58, pp. 525-527.

Lee, Y., et al. "Discovery of a small molecule that inhibits the interaction of anthrax edema factor with its cellular activator, calmodulin", Chemistry & Biology (2004), vol. 11, pp. 1139-1146.

Little, S. F., et al., "Structure-function analysis of *Bacillus anthracis* edema factor by using monoclonal antibodies", Biochemical and Biophysical Research Communication (1994), vol. 199:2, pp. 676-682.

Mouallem, M. et al., "*Bordetella pertussis* Adenylate Cyclase Toxin: Intoxication of Host Cells by Bacterial Invasion", Infection and Immunity (1990), vol. 58:11, pp. 3759-3764.

Onkol, T. et al., "Antimicrobial Activities of some (2-Benzimidazolythiojacetorydrazide) Derivatives", Gazi University Eczacilik Fakultes Ankara, J. Fac. Pharm. Gazi (1992), vol. 9:1, pp. 47-57.

Paccani, S.R. "Anthrax toxins suppress T lymphocyte activation by disrupting antigen receptor signaling", J. of Experimental Medicine (2005), vol. 201:3, pp. 325-331.

Peterkofsky, A. et al., "Glucose Inhibition of Adenylate Cyclase in Intact Cells of *Escherichia coli* B", PNAS USA (1974), vol. 71:6, pp. 2324-2328.

Saini, S.S. et al., "The Cox-2-Specific Inhibitor Celecoxib Inhibits Adenylyl Cyclase", Inflammation (2003), vol. 27:2, pp. 79-88.

Shen, Y. et al., "Selective inhibition of anthrax edema factor by adefovir, a drug for chronic hepatitis B virus infection" PNAS USA (2004), vol. 101:9, pp. 3242-3247.

Shoshani, I. et al., "Inhibition of Adenylyl Cyclase by Acyclic Nucleoside Phosphonate Antiviral Agents", J. Biological Chemistry (1999), vol. 274:49, pp. 34742-34744.

Soelaiman, S., et al., "Structure-based inhibitor discovery against adenylyl cyclase toxins from pathogenic bacteria that cause anthrax and whooping cough", J. Biological Chemistry (2003) vol. 278:28, pp. 2599-25997.

Steegborn, C. et al., "A Novel Mechanism for Adenylyl Cyclase Inhibition from the Crystal Structure of its Complex with Catechol Estrogen", J. of Biological Chemistry (2005), vol. 280:36, pp. 31754-31759.

Stipa, G. et al., "Sporadic amyotrophic lateral sclerosis as an infectious disease: A possible role of cyanobacteria?", Medical Hypothesis (2006), vol. 67, pp. 1363-1371.

Tillman H.L. et al., "Successful Treatment of Fibrosing Cholestatic Hepatitis Using Adefovir Dipivoxil in a Patient With Cirrhosis and Renal Insufficiency" Liver Transplantation (2003), vol. 9:2, pp. 191-196.

Ausubel, F. M et al Eds., Current Protocols in Molecular Biology (1987), John Wiley & Sons, Inc., Publishers, USA (Table of Contents).

Cann, M.J. et al., "A Defined Subset of Adenylyl Cyclases Is Regulated by Bicarbonate Ion", J. Biological Chemistry (2003), vol. 278:37, pp. 35033-35038.

Cann, M.J., Signalling Through Cyclic Nucleotide Monophosphates in Cyanobacteria, New Phytologist (2003), vol. 161, pp. 23-34.

Carter, R. et al., "Plasmodia of Rodents", ch. 8, pp. 359-465 in Parasitic Protozoa (1977), Academic Press, Publishers, USA.

Chien, M. et al., "The Genomic Sequence of the Accidental Pathogen *Legionella pneumophila*", Science (2004), vol. 305, pp. 1966-1968.

Church, D.C., Livestock Feeds and Feeding (1977), D.C. Church, Publisher, USA (Table of Contents).

Cornelis, G. R. et al., "Assembly and Function of Type III Secretory Systems" Annu. Rev. Microbiol (2000), vol. 54, pp. 735-774.

Cramton, E.W. et al., Applied Animal Nutrition: The use of Feedstuffs in the Formulation of Livestock Rations, (2nd ed. 1961), W.H. Freeman and Company, Publishers, USA (Table of Contents).

Dolin, P.J. et al., "Global Tuberculosis Incidence and Mortality During 1990-2000", Bul. of the WHO (1994), vol. 72:2, pp. 213-220.

Galán, J.E. et al., "Type III Secretion Machines: Bacterial Devices for Protein Delivery into Host Cells", Science (1999), vol. 284, pp. 1322-1328.

Gennaro, A. R ed., Remington's Pharmaceuticals Sciences, Practice of the Science and Pharmacy ( 1995), Mack Publishing Company, Publishers, USA (Table of Contents).

Harper, J.F. et al., "Femtomole Sensitive Radioimmunoassay for Cyclic AMP and Cyclic GMP After 2'0 Acetylation by Acetic Anhydride in Aqueous Solution", J. Cyclic Nuc. Res. (1975), vol. 1:1, pp. 207-218.

Jonas D. et al., "Development and Mechanism of Fluoroquinolone Resistance in *Legionella pneumophila*" JAC (2003), vol. 51, pp. 275-280.

Kamenetsky, M. et al., "Molecular Details of cAMP Generation in Mammalian Cells: A Tale of Two Systems", J. Mol. Biol. (2006), vol. 362, pp. 623-639.

Kozliak, E.I. et al., "Role of Bicarbonate/CO2 in the Inhibition of *Escherichia coli* Growth by Cyanate", J. Bacteriology (1995), vol. 177:11, pp. 3213-3129.

Lathem, W.W. et al., "Progression of Primary Pneumonic Plague: A Mouse Model of Infection, Pathology, and Bacterial Transcriptional Activity", PNAS (2005), vol. 102:49, pp. 17786-17791.

Litvin, T.N. et al., "Kinetic Properties of "Soluble" Adenylyl Cyclase", J. Biological Chemistry (2003), vol. 278:18, pp. 15922-15926.

Lowrie, D.B. et al., "Mycobacterium Microti May Protect Itself From Intracellular Destruction by Releasing Cyclic AMP into Phagosomes", Nature (1975), vol. 254, pp. 600-602.

Lowrie, D.B. et al., "Phagosome-Lysosome Fusion and Cyclic Adenosine 3':5'-Monophosphate in Macrophages Infected with *Mycobacterium microti*, *Mycobacterium bovis* BCG or *Mycobacterium lepraemrium*" JGM (1979), vol. 110, pp. 431-441.

Nicoloff, H. et al., "Repression of the pyr Operon in *Lactobacillus plantarum* Prevents Its Ability to Grow at Low Carbon Dioxide Levels" JB (2005), vol. 187:6, pp. 2093-2104.

Nordstedt, C. et al., "A Modification of a Protein-Binding Method for Rapid Quantification of cAMP in Cell-Culture Supernatants and Body Fluid", Anal. BioChem (1990), vol. 186, pp. 231-234.

Rajagopal, M. et al., "Low Pressure Co2 Storage of Raw Milk: Microbiological Effects", J. Dairy Sci. (2005), vol. 88, pp. 3130-3138.

Salomon, Y. et al., "A Highly Sensitive Adenylate Cyclase Assay", Anal. BioChem. (1974), vol. 58, pp. 541-548.

Sambrook, J. et al., eds. Molecular Cloning: A Laboratory Manua, (2nd ed. 1989), Cold Spring Harbor Laboratory Press, Publishers, USA (Table of Contents).

Savkovic, S.D. et al., "Mouse Model of Enteropathogenic *Escherichia coli* Infection", Infection and Immunity (2005), vol. 73:2, pp. 1161-1170.

Savkovic, S.D. et al., "Attachment of a Noninvasive Enteric Pathogen, Enteropathogenic *Escherichia coli*, to Cultured Human Intestinal Epithelial Monolayers Induces Transmigration of Neutrophils", Infection and Immunity (1996), vol. 64:11, pp. 4480-4487.

Siles-Lucs, M. et al., "Cestode Parasites: Application of In Vivo and In Vitro Models for Studies on the Host-Parasite Relationship" Advances in Parasitology (2002), vol. 51, pp. 133-230.

Steiner, A. et al., "Radioimmunoassay for the Measurement of Adenosine 3',5'-Cylic Phosphate", PNAS (1969), vol. 64, pp. 367-373.

(56) References Cited

OTHER PUBLICATIONS

Vassella, E. et al., "Differentiation of African Trypanosomes is Controlled by a Density Sensing Mechanism Which Signals Cell Cycle Arrest via the cAMP Pathway", J. Cell Science (1997), vol. 110, pp. 2661-2671.

Wolfgang, M.C. et al., "Coordinate Regulation of Bacterial Virulence Genes by a Novel Adenylate Cyclase-Dependent Signaling Pathway", Dev. Cell (2003), vol. 4, pp. 253-263.

* cited by examiner

ADENYLYL CYCLASES AS NOVEL TARGETS FOR THE TREATMENT OF INFECTION BY EUKARYOTIC PATHOGENS

CROSS REFERENCE TO RELATED APPLICATIONS

The present application claims the benefit of the following U.S. Provisional Patent Application No. 60/880,089, filed Jan. 12, 2007. The contents of this applications is incorporated herein by reference.

FEDERAL FUNDING

This invention was made with government support under contract numbers AI64842, GM62328and HD42060 awarded by NIH. The government has certain rights in the invention.

FIELD OF THE INVENTION

The present invention relates to a method of preventing or treating a disease caused by infection by a eukaryotic pathogen by administering an effective amount of a modulator of adenylyl cyclase. The invention also provides pharmaceutical compositions useful for preventing or treating a disease, with the compositions containing a therapeutically effective amount of a modulator of an adenylyl cyclase of the eukaryotic pathogen. The invention also provides screening methods for identifying selective modulators of a eukaryotic pathogen's adenylyl cyclase that do not substantially modulate adenylyl cyclase of the subject. The invention also provides methods for culturing eukaryotic pathogens and methods for inducing the pathogenic state in vitro.

BACKGROUND OF THE INVENTION

Cyclic-3',5'-adenosine monophosphate (cAMP) mediates cellular responses to nutritional conditions and extracellular conditions in organisms from bacteria to humans. Cyclic AMP is synthesized from adenosine triphospate (ATP) by adenylyl cyclase, and it is rapidly destroyed by cyclic AMP phosphodiesterases that hydrolyze cAMP to form adenosine 5'-monophosphate (5'-AMP). In a non-responding cell, a basal level of cAMP synthesis is balanced by the rate of its breakdown. The concentration of cyclic AMP inside a cell can change by more than twenty fold in seconds in response to extracellular signals. These rapid responses arise because the activity of the adenylyl cyclase is stimulated such that synthesis of the molecule overwhelms this normal (usually static) rate of breakdown.

Adenylyl cyclase (AC) is a group of enzymes that catalyze the conversion of ATP to cAMP and pyrophosphate. Six classes of adenylyl cyclase enzymes have been identified based upon protein sequence and properties. Class I adenylyl cyclases are found primarily in enteric bacteria. Class II adenylyl cyclases include the toxins secreted by pathogens such as edema factor (EF) from *Bacillus anthracis* (which causes anthrax), CyaA from *Bordetella pertussis* (the cause of whooping cough), and ExoY from *Pseudomonas aeruginosa* (the cause of various nosocomial infections). Class III is the largest known group and consists of cyclases found in bacteria, archaea and eukaryotes. The class IV enzymes are found in archaeal organisms, and also in some bacteria including the plague-causing *Yersinia pestis*. Class V is comprised of adenylyl cyclase from the strict anaerobic bacterium *Prevotella ruminicola*. Class VI is found in the nitrogen fixing bacteria *Rhizobium etli*. All six classes of enzymes are present in bacteria, while only enzymes belonging to class III have been described in eukaryotes.

In mammalian cells, cAMP is produced by two related families of class III adenylyl cyclase, transmembrane adenylyl cyclases (tmAC) and soluble adenylyl cyclases (sAC). These two families differ in sub-cellular localization, and respond to different regulators (for a review see Kamenetsky et al., *J. Mol. Biol.* Vol. 362, pp. 623-39, 2006). The primary regulators for tmACs are hetrotrimeric G proteins, which transmit extracellular signals via G protein-coupled receptors in response to hormonal stimuli. In contrast, sACs are regulated by intracellular bicarbonate and calcium.

During pathogenesis in a host, an infecting organism is challenged to respond to a diverse and dynamic set of environmental conditions. A variety of pathogens exploit this dramatic environmental shift as a signal to alter their growth and virulence. For example, there is a 150-fold difference in $CO_2$ concentration inside the human (or animal) body (5% $CO_2$) compared to the atmosphere (0.03% $CO_2$). When infectious micro-organisms sense this difference, they tailor their genetic program to one suitable for being inside an infectible host.

SUMMARY OF THE INVENTION

In one aspect, the present invention features a method for the treatment of a subject with a disease caused the infection by a eukaryotic pathogen by administering to the subject a therapeutic amount of a modulator of an adenylyl cyclase of the eukaryotic pathogen.

The invention also provides a method for the treatment of a subject with a disease caused by infection by a eukaryotic pathogen by administering to the subject a therapeutic amount of a modulator of a pathogen's adenylyl cyclase, wherein the amount of the modulator administered is effective at substantially preventing the pathogen from changing to a pathogenic state from a non-pathogenic state, or wherein the amount of modulator of the pathogen's adenylyl cyclase administered is effective to cause the pathogen to substantially revert to a non-pathogenic state from a pathogenic state. Preventing eukaryotic pathogens from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, capsule production, and changes in growth rate.

The invention also provides a method for the treatment of a subject with a disease caused by infection by eukaryotic pathogen, by administering to the subject a therapeutic amount of a modulator of the pathogen's adenylyl cyclase, wherein the modulator of the pathogen's adenylyl cyclase inhibits the pathogen's adenylyl cyclase. In other embodiments, the modulator activates the pathogen's adenylyl cyclase.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase has a substantially biocidal effect upon the infecting pathogen. In other embodiments the modulator of the pathogen's adenylyl cyclase has a substantially biostatic effect upon the infecting pathogen. In certain embodiments, the amount of modulator of the pathogen's adenylyl cyclase does not substantially kill the infecting pathogen. In other embodiments, the amount of modulator of the pathogen's adenylyl cyclase does not inhibit or prevent the growth of the pathogen.

The invention also provides a method for the treatment of a subject with a disease caused by, infection by a eukaryotic pathogen, by administering to the subject a therapeutic amount of a modulator of the pathogen's adenylyl cyclase, wherein the modulator of the pathogen's adenylyl cyclase affects more than one adenylyl cyclase of an infecting pathogen. The invention also provides that the modulator of the pathogen's adenylyl cyclase affects more than one adenylyl cyclase of more than one infecting pathogen.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase affects the response of the infecting pathogen's adenylyl cyclase to $CO_2$. In other embodiments, the modulator affects the response of the infecting pathogen's adenylyl cyclase to $HCO_3$. In other embodiments, the modulator affects the response of the infecting pathogen's adenylyl cyclase to pH.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase affects a Class III adenylyl cyclase.

The invention also provides a method for the treatment of a subject with a disease caused by infection by a eukaryotic pathogen, by administering to the subject a therapeutic amount of a modulator of the pathogen's adenylyl cyclase, wherein the infection is caused by a pathogen that is resistant to one or more anti-microbial agents.

The invention also provides a method for the treatment of a subject with a disease caused by infection by a eukaryotic pathogen, by administering to the subject a therapeutic amount of a modulator of the pathogen's adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for the treatment of a subject with a disease caused by infection by a eukaryotic pathogen, by administering to the subject a therapeutic amount of a modulator of the pathogen's adenylyl cyclase, wherein the subject is a human.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase does not substantially inhibit the adenylyl cyclases of the subject. In this embodiment, the modulator of the pathogen's adenylyl cyclase is selective relative to subject's adenylyl cyclase(s). Preferably, the modulator of the pathogen's adenylyl cyclase is sufficiently selective against the subject's adenylyl cyclase that a therapeutic effect upon the infecting pathogen can be achieved without toxic regulation of the subject's adenylyl cyclase occurring.

The invention also provides a method of treating an infection by a eukaryotic pathogen in a subject, mediated by adenylyl cyclase of a pathogen in a subject, comprising, modulating the adenylyl cyclase of the eukaryotic pathogen.

The invention also provides a method of inhibiting the adenylyl cyclase of a eukaryotic pathogen, the method comprising contacting eukaryotic cells with a compound that inhibits adenylyl cyclase of the eukaryotic pathogen.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase is selected from the group consisting of small molecules, aptamers, and interfering RNA.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase is selected from the group consisting of one or more compounds selected from Table 1.

The invention also provides a method for the treatment of a subject with a disease caused by infection by a eukaryotic pathogen, by administering to the subject a therapeutic amount of a modulator of the pathogen's adenylyl cyclase, wherein the modulator of the pathogen's adenylyl cyclase is selected from catechol estrogens and derivatives thereof.

The invention also provides a method for the treatment of a subject with a disease caused by infection by a eukaryotic pathogen, by administering to the subject a therapeutic amount of a modulator of the pathogen's adenylyl cyclase in combination with one or more additional therapeutic agents. In a further embodiment, the additional therapeutic agent is an anti-microbial agent.

In one aspect, the present invention features a method for the treatment of a subject with a disease caused the infection by a fungus by administering to the subject a therapeutic amount of a modulator of a fungal adenylyl cyclase.

The invention also provides a method for the treatment of a subject with a disease caused by infection by fungus by administering to the subject a therapeutic amount of a modulator of a fungal adenylyl cyclase, wherein the amount of the modulator administered is effective at substantially preventing the fungus from changing to a pathogenic state from a non-pathogenic state, or wherein the amount of modulator of the fungal adenylyl cyclase administered is effective to cause the fungus to substantially revert to a non-pathogenic state from a pathogenic state. Preventing a fungus from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, capsule production, and changes in growth rate.

The invention also provides a method for the treatment of a subject with a disease caused by infection by a fungus, by administering to the subject a therapeutic amount of a modulator of a fungal adenylyl cyclase, wherein the modulator of the fungal adenylyl cyclase inhibits the fungal adenylyl cyclase. In other embodiments, the modulator activates the fungal adenylyl cyclase.

The invention also provides a method for the treatment of a subject with a disease caused by infection by a fungus, by administering to the subject a therapeutic amount of a modulator of a fungal adenylyl cyclase, wherein the modulator of the fungal adenylyl cyclase has a substantially fungicidal effect upon the infecting fungus. In other embodiments the modulator of the fungal adenylyl cyclase has a substantially biostatic effect upon the infecting fungus. In certain embodiments, the amount of modulator of the fungal adenylyl cyclase does not substantially kill the infecting fungus. In other embodiments, the amount of modulator of the fungal adenylyl cyclase does not inhibit or prevent the growth of the fungus.

The invention also provides a method for the treatment of a subject with a disease caused by infection by a fungus, by administering to the subject a therapeutic amount of a modulator of the fungal adenylyl cyclase, wherein the modulator of the fungal adenylyl cyclase affects more than one adenylyl cyclase of an infecting fungus. The invention also provides that the modulator of the fungal adenylyl cyclase affects more than one adenylyl cyclase of more than one infecting fungus.

The invention also provides a method for the treatment of a subject with a disease caused by infection by a fungus, by administering to the subject a therapeutic amount of a modulator of a fungal adenylyl cyclase, wherein the modulator of fungal adenylyl cyclase affects the response of the fungal adenylyl cyclase to $CO_2$. In other embodiments, the modulator affects the response of the fungal adenylyl cyclase to $HCO_3$. In other embodiments, the modulator affects the response of the fungal adenylyl cyclase to pH.

The invention also provides a method for the treatment of a subject with a disease caused by infection by a fungus, by administering to the subject a therapeutic amount of a modulator of fungal adenylyl cyclase, wherein the fungal adenylyl cyclase is a Class III adenylyl cyclase.

The invention also provides a method for the treatment of a subject with a disease caused by infection by a fungus, by administering to the subject a therapeutic amount of a modulator of fungal adenylyl cyclase, wherein the infection is caused by a fungus that is resistant to one or more anti-fungal agents.

The invention also provides a method for the treatment of a subject with a disease caused by infection by a fungus, by administering to the subject a therapeutic amount of a modulator of fungal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for the treatment of a subject with a disease caused by infection by a fungus, by administering to the subject a therapeutic amount of a modulator of the fungal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for the treatment of a subject with a disease caused by infection by a fungus, by administering to the subject a therapeutic amount of a modulator of fungal adenylyl cyclase, wherein the modulator of the fungal adenylyl cyclase does not substantially inhibit the adenylyl cyclases of the subject. In this embodiment, the modulator of the fungal adenylyl cyclase is selective relative to subject's adenylyl cyclase(s). Preferably, the modulator of the fungal adenylyl cyclase is sufficiently selective against the subject's adenylyl cyclase that a therapeutic effect upon the infecting fungus can be achieved without toxic regulation of the subject's adenylyl cyclase occurring.

The invention also provides a method of treating an infection by a fungus in a subject, mediated by fungal adenylyl cyclase in a subject, comprising, modulating the adenylyl cyclase of the fungus.

The invention also provides a method of inhibiting the adenylyl cyclase of a fungus, the method comprising contacting eukaryotic cells with a compound that inhibits adenylyl cyclase of the fungus.

The invention also provides a method for the treatment of a subject with a disease caused by infection by a fungus, by administering to the subject a therapeutic amount of a modulator of fungal adenylyl cyclase, wherein the modulator of fungal adenylyl cyclase is selected from the group consisting of small molecules, aptamers, and interfering RNA.

The invention also provides a method for the treatment of a subject with a disease caused by infection by a fungus, by administering to the subject a therapeutic amount of a modulator of fungal adenylyl cyclase, wherein the modulator of adenylyl cyclase is a quorum sensing molecule or a derivative of a quorum sensing molecule. In one embodiment, the quorum sensing molecule is farnesol or a derivative thereof. In another embodiment, the quorum sensing molecule is N-3-oxo-C12 homoserine lactone or a derivative thereof.

The invention also provides a method for the treatment of a subject with a disease caused by infection by a fungus, by administering to the subject a therapeutic amount of a modulator of a fungal adenylyl cyclase, wherein the modulator of the fungal adenylyl cyclase is selected from catechol estrogens and derivatives thereof.

The invention also provides a method for the treatment of a subject with a disease caused by infection by a fungus, by administering to the subject a therapeutic amount of a modulator of a fungal adenylyl cyclase, wherein the modulator of the fungal adenylyl cyclase is selected from the group consisting of one or more compounds selected from Table 1.

The invention also provides a method for the treatment of a subject with a disease caused by infection by a fungus, by administering to the subject a therapeutic amount of a modulator of fungal adenylyl cyclase, wherein the amount of inhibitor of adenylyl cyclase administered is effective at substantially preventing the fungus from changing to a filamentous state from a non-filamentous state, or wherein the amount of inhibitor of adenylyl cyclase administered is effective to cause the fungus to substantially revert to a non-filamentous state from a filamentous state.

The invention also provides a method for the treatment of a subject with a disease caused by infection by a fungus, by administering to the subject a therapeutic amount of a modulator of fungal adenylyl cyclase, wherein the infection is superficial, cutaneous, subcutaneous and/or systemic.

The invention also provides a method for the treatment of a subject with a disease caused by infection by a fungus, by administering to the subject a therapeutic amount of a modulator of fungal adenylyl cyclase, wherein the fungus is selected from the group consisting of yeasts and moulds.

The invention also provides a method for the treatment of a subject with a disease caused by infection by a fungus, by administering to the subject a therapeutic amount of a modulator of fungal adenylyl cyclase, wherein the fungus is from a genus selected from the group consisting of *Candida, Cryptococcus, Filobasidiella, Geotrichum, Issatchenkia, Malassezia, Pichia, Pneumocystis, Rhodotorula, Trichosporon, Absidia, Ajellomyces, Arthroderma, Aspergillus, Blastomyces, Cladophialophora, Coccidioides, Epidermophyton, Entomophthorales, Exophiala, Fonsecaea, Fusarium, Histoplasma, Hortaea, Madurella, Microsporum, Mucor, Nectria, Paecilomyces, Paracoccidioides, Penicillium, Pseudallescheria, Rhizopus, Scedosporium, Sporothrix,* and *Trichophyton.*

The invention also provides a method for the treatment of a subject with a disease caused by infection by a fungus, by administering to the subject a therapeutic amount of a modulator of fungal adenylyl cyclase, wherein the fungus is selected from the group consisting of *Candida albicans, Candida glabrata, Candida guilliermondii, Candida krusei, Candida parapsilosis, Candida tropicalis, Cryptococcus neoformans, Filobasidiella neoformans, Geotrichum candidum, Issatchenkia orientalis, Malassezia furfur, Malassezia pachydermatis, Pichia anomala, Pichia guilliermondii, Pneumocystis carinii, Rhodotorula mucilaginosa, Trichosporon asahii, Trichosporon cutaneum, Trichosporon inkin, Trichosporon mucoides, Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigatus, Aspergillus niger, Blastomyces dermatitidis, Cladophialophora carrionii, Coccidioides immitis, Epidermophyton floccosum, Exophiala dermatitidis, Fonsecaea pedrosoi, Fusarium solani, Histoplasma capsulatum, Histoplasma duboisii, Hortaea werneckii, Madurella grisae, Microsporum canis, Microsporum fulvum, Microsporum gypseum, Mucor circinelloides, Nectria haematococca, Paecilomyces variotii, Paracoccidioides brasiliensis, Penicillium marneffei, Pseudallescheria boydii, Rhizopus arrhizus, Rhizopus oryzae, Rhizomucor pusillus, Scedosporium apiospermum, Schizophyllum commune, Sporothrix schenckii, Trichophyton mentagrophytes, Trichophyton rubrum*, and *Trichophyton verrucosum.*

In a preferred embodiment the invention also provides a method for the treatment of a subject with a disease caused by infection by a fungus, by administering to the subject a therapeutic amount of a modulator of fungal adenylyl cyclase, wherein the fungus is selected from the group consisting of *Candida albicans, Candida glabrata, Cryptococcus neoformans, Aspergillus fumigatus, Coccidioides, Histoplasma, Blastomyces,* and *Paracoccidioides.*

The invention also provides a method for the treatment of a subject with a disease caused by infection by a fungus, by administering to the subject a therapeutic amount of a modulator of fungal adenylyl cyclase in combination with one or more additional therapeutic agents. In a further embodiment, the additional therapeutic agent is an anti-fungal agent.

In one aspect, the present invention features a method for the treatment of a subject with a disease caused by infection by a protozoan by administering to the subject a therapeutic amount of a modulator of a protozoal adenylyl cyclase.

The invention also provides a method for the treatment of a subject with a disease caused by infection by a protozoan by administering to the subject a therapeutic amount of the modulator of a protozoal adenylyl cyclase, wherein the amount of the modulator administered is effective at substantially preventing the protozoan from changing to a pathogenic state from a non-pathogenic state, or wherein the amount of modulator of the protozoal adenylyl cyclase administered is effective to cause the protozoan to substantially revert to a non-pathogenic state from a pathogenic state. Preventing a protozoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, excystation, and changes in growth rate.

The invention also provides a method for the treatment of a subject with a disease caused by infection by a protozoan, by administering to the subject a therapeutic amount of a modulator of a protozoal adenylyl cyclase, wherein the modulator of the protozoal adenylyl cyclase inhibits the protozoal adenylyl cyclase. In other embodiments, the modulator activates the protozoal adenylyl cyclase.

The invention also provides a method for the treatment of a subject with a disease caused by infection by a protozoan, by administering to the subject a therapeutic amount of a modulator of a protozoal adenylyl cyclase, wherein the modulator of the protozoal adenylyl cyclase has a substantially kills the infecting protozoan. In other embodiments the modulator of the pathogen's adenylyl cyclase has a substantially biostatic effect upon the infecting protozoan. In certain embodiments, the amount of modulator of the protozoal adenylyl cyclase does not substantially kill the infecting protozoan. In other embodiments, the amount of modulator of the protozoal adenylyl cyclase does not inhibit or prevent the growth of the protozoan.

The invention also provides a method for the treatment of a subject with a disease caused by infection by a protozoan, by administering to the subject a therapeutic amount of a modulator of the protozoal adenylyl cyclase, wherein the modulator of the protozoal adenylyl cyclase affects more than one adenylyl cyclase of an infecting protozoan. The invention also provides that the modulator of the protozoal adenylyl cyclase affects more than one adenylyl cyclase of more than one infecting protozoan.

The invention also provides a method for the treatment of a subject with a disease caused by infection by a protozoan, by administering to the subject a therapeutic amount of a modulator of a protozoal adenylyl cyclase, wherein the modulator of protozoal adenylyl cyclase affects the response of the protozoal adenylyl cyclase to $CO_2$. In other embodiments, the modulator affects the response of the protozoal adenylyl cyclase to $HCO_3$. In other embodiments, the modulator affects the response of the protozoal adenylyl cyclase to pH.

The invention also provides a method for the treatment of a subject with a disease caused by infection by a protozoan, by administering to the subject a therapeutic amount of a modulator of protozoal adenylyl cyclase, wherein the protozoal adenylyl cyclase is a Class III adenylyl cyclase.

The invention also provides a method for the treatment of a subject with a disease caused by infection by a protozoan, by administering to the subject a therapeutic amount of a modulator of protozoal adenylyl cyclase, wherein the infection is caused by a protozoan that is resistant to one or more antiprotozoal agents.

The invention also provides a method for the treatment of a subject with a disease caused by infection by a protozoan, by administering to the subject a therapeutic amount of a modulator of protozoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for the treatment of a subject with a disease caused by infection by a protozoan, by administering to the subject a therapeutic amount of a modulator of the protozoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for the treatment of a subject with a disease caused by infection by a protozoan, by administering to the subject a therapeutic amount of a modulator of protozoal adenylyl cyclase, wherein the modulator of the protozoal adenylyl cyclase does not substantially inhibit the adenylyl cyclases of the subject. In this embodiment, the modulator of the protozoal adenylyl cyclase is selective relative to subject's adenylyl cyclase(s). Preferably, the modulator of the protozoal adenylyl cyclase is sufficiently selective against the subject's adenylyl cyclase that a therapeutic effect upon the infecting protozoan can be achieved without toxic regulation of the subject's adenylyl cyclase occurring.

The invention also provides a method of treating an infection by a protozoan in a subject, mediated by protozoal adenylyl cyclase in a subject, comprising modulating the adenylyl cyclase of the protozoan.

The invention also provides a method of inhibiting the adenylyl cyclase of a protozoan, the method comprising contacting eukaryotic cells with a compound that inhibits adenylyl cyclase of the protozoan.

The invention also provides a method for the treatment of a subject with a disease caused by infection by, a protozoan, by administering to the subject a therapeutic amount of a modulator of protozoal adenylyl cyclase, wherein the modulator of protozoal adenylyl cyclase is selected from the group consisting of small molecules, aptamers, and interfering RNA.

The invention also provides a method for the treatment of a subject with a disease caused by infection by a protozoan, by administering to the subject a therapeutic amount of a modulator of the protozoal adenylyl cyclase, wherein the modulator of the protozoal adenylyl cyclase is selected from catechol estrogens and derivatives thereof.

The invention also provides a method for the treatment of a subject with a disease caused by infection by a protozoan, by administering to the subject a therapeutic amount of a modulator of a protozoal adenylyl cyclase, wherein the modulator of the protozoal adenylyl cyclase is selected from the group consisting of one or more compounds selected from Table 1.

The invention also provides a method for the treatment of a subject with a disease caused by infection by a protozoan, by administering to the subject a therapeutic amount of a modulator of a protozoal adenylyl cyclase, wherein the protozoan is selected from the group consisting of Sarcodina, Ciliophora, Mastigophora, and Sporozoa.

The invention also provides a method for the treatment of a subject with a disease caused by infection by a protozoan, by administering to the subject a therapeutic amount of a modulator of a protozoal adenylyl cyclase, wherein the protozoan is selected from the order gregarinia, coccidia, haemosporidia, and piroplasmida.

The invention also provides a method for the treatment of a subject with a disease caused by infection by a protozoan, by administering to the subject a therapeutic amount of a modulator of a protozoal adenylyl cyclase, wherein the protozoan is selected from the group consisting of: *Acanthamoeba castellanii, Babesia bigemina, Babesia canis, Babesia divergens, Babesia microti, Balantidium coli, Besnoitia besnoiti, Cryptosporidium parvum, Cyclospora cayetensis, Eimeria acervulina, Eimeria bovis, Eimeria brunetti, Eimeria carpelli, Eimeria cyprinorum, Eimeria irresidua, Eimeria magna, Eimeria maxima, Eimeria mitis, Eimeria necatrix, Eimeria nieschulzi, Eimeria perforans, Eimeria phasiani, Eimeria praecox, Eimeria stiedae, Eimeria tenella, Eimeria truncata, Eimeria zurmii, Entamoeba histolytica, Giardia Lamblia, Leishmania donovani, Microsporidia, Naeglaria flowleri, Plasmodium falciparum, Plasmodium malariae, Plasmodium ovale, Plasmodium vivax, Pneumocystis carinii, Sarcocystis neurona, Sarcocystis tenella, Toxoplasma gondii, Trichomonas vaginalis, Trypanosoma brucei,* and *Trypanosoma cruzi.*

The invention also provides a method for the treatment of a subject with a disease caused by infection by a protozoan, by administering to the subject a therapeutic amount of a modulator of protozoal adenylyl cyclase in combination with one or more additional therapeutic agents. In a further embodiment, the additional therapeutic agent is an anti-protozoal agent.

In one aspect, the present invention features a method for the treatment of a subject with a disease caused by infection by a metazoan by administering to the subject a therapeutic amount of a modulator of a metazoal adenylyl cyclase.

The invention also provides a method for the treatment of a subject with a disease caused by infection by a metazoan by administering to the subject a therapeutic amount of the modulator of a metazoal adenylyl cyclase, wherein the amount of the modulator administered is effective at substantially preventing the metazoan from changing to a pathogenic state from a non-pathogenic state, or wherein the amount of modulator of the metazoal adenylyl cyclase administered is effective to cause the metazoan to substantially revert to a non-pathogenic state from a pathogenic state. Preventing a metazoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a method for the treatment of a subject with a disease caused by infection by a metazoan, by administering to the subject a therapeutic amount of a modulator of a metazoal adenylyl cyclase, wherein the modulator of the metazoal adenylyl cyclase inhibits the metazoal adenylyl cyclase. In other embodiments, the modulator activates the metazoal adenylyl cyclase.

The invention also provides a method for the treatment of a subject with a disease caused by infection by a metazoan, by administering to the subject a therapeutic amount of a modulator of a metazoal adenylyl cyclase, wherein the modulator of the metazoal adenylyl cyclase has a substantially biocidal effect on the infecting metazoan. In other embodiments the modulator of the pathogen's adenylyl cyclase has a substantially biostatic effect upon the infecting metazoan. In certain embodiments, the amount of modulator of the metazoal adenylyl cyclase does not substantially kill the infecting metazoan. In other embodiments, the amount of modulator of the metazoal adenylyl cyclase does not inhibit or prevent the growth of the metazoan.

The invention also provides a method for the treatment of a subject with a disease caused by infection by a metazoan, by administering to the subject a therapeutic amount of a modulator of the metazoal adenylyl cyclase, wherein the modulator of the metazoal adenylyl cyclase affects more than one adenylyl cyclase of an infecting metazoan.

The invention also provides that the modulator of the metazoal adenylyl cyclase affects more than one adenylyl cyclase of more than one infecting metazoan.

The invention also provides a method for the treatment of a subject with a disease caused by infection by a metazoan, by administering to the subject a therapeutic amount of a modulator of a metazoal adenylyl cyclase, wherein the modulator of metazoal adenylyl cyclase affects the response of the metazoal adenylyl cyclase to $CO_2$. In other embodiments, the modulator affects the response of the metazoal adenylyl cyclase to $HCO_3$. In other embodiments, the modulator affects the response of the metazoal adenylyl cyclase to pH.

The invention also provides a method for the treatment of a subject with a disease caused by infection by a metazoan, by administering to the subject a therapeutic amount of a modulator of metazoal adenylyl cyclase, wherein the metazoal adenylyl cyclase is a Class III adenylyl cyclase.

The invention also provides a method for the treatment of a subject with a disease caused by infection by a metazoan, by administering to the subject a therapeutic amount of a modulator of a metazoal adenylyl cyclase, wherein the infection is caused by a metazoan that is resistant to one or more anti-metazoal agents.

The invention also provides a method for the treatment of a subject with a disease caused by infection by a metazoan, by administering to the subject a therapeutic amount of a modulator of metazoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for the treatment of a subject with a disease caused by infection by a metazoan, by administering to the subject a therapeutic amount of a modulator of the metazoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for the treatment of a subject with a disease caused by infection by a metazoan, by administering to the subject a therapeutic amount of a modulator of metazoal adenylyl cyclase, wherein the modulator of the metazoal adenylyl cyclase does not substantially inhibit the adenylyl cyclases of the subject. In this embodiment, the modulator of the metazoal adenylyl cyclase is selective relative to subject's adenylyl cyclase(s). Preferably, the modulator of the metazoal adenylyl cyclase is sufficiently selective against the subject's adenylyl cyclase that a therapeutic effect upon the infecting metazoan can be achieved without toxic regulation of the subject's adenylyl cyclase occurring.

The invention also provides a method of treating an infection by a metazoan in a subject, mediated by a metazoal adenylyl cyclase in a subject, comprising modulating the adenylyl cyclase of the metazoan.

The invention also provides a method of inhibiting the adenylyl cyclase of a metazoan, the method comprising contacting eukaryotic cells with a compound that inhibits adenylyl cyclase of the metazoan.

The invention also provides a method for the treatment of a subject with a disease caused by infection by a metazoan, by administering to the subject a therapeutic amount of a modulator of metazoal adenylyl cyclase, wherein the modulator of metazoal adenylyl cyclase is selected from the group consisting of small molecules, aptamers, and interfering RNA.

The invention also provides a method for the treatment of a subject with a disease caused by infection by a metazoan, by administering to the subject a therapeutic amount of a modulator of the metazoal adenylyl cyclase, wherein the modulator of the metazoal adenylyl cyclase is selected from catechol estrogens and derivatives thereof.

The invention also provides a method for the treatment of a subject with a disease caused by infection by a metazoan, by administering to the subject a therapeutic amount of a modulator of a metazoal adenylyl cyclase, wherein the modulator of the metazoal adenylyl cyclase is selected from the group consisting of one or more compounds selected from Table 1.

The invention also provides a method for the treatment of a subject with a disease caused by infection by a metazoan, by administering to the subject a therapeutic amount of a modulator of a metazoal adenylyl cyclase, wherein the metazoan is selected from the group consisting of Nematodes, Cestodes, and Trematodes.

The invention also provides a method for the treatment of a subject with a disease caused by infection by a metazoan, by administering to the subject a therapeutic amount of a modulator of a metazoal adenylyl cyclase, wherein the metazoan is selected from the group consisting of *Taenia solium, Taenia saginata, Diphyllobothrium latum, Echniococcus granulosus, Schistosomiasis, Clonorchis, Enterobius, Tichuris, Ascaris, Ancylostoma, Strongyloides, Trichinella, Anisakis, Wuchereria, Onchocerca, Loa, Dracuncululs,* and *Toxocara.*

The invention also provides a method for the treatment of a subject with a disease caused by infection by a metazoan, by administering to the subject a therapeutic amount of a modulator of metazoal adenylyl cyclase in combination with one or more additional therapeutic agents. In a further embodiment, the additional therapeutic agent is an anti-metazoal agent.

In one aspect, the present invention features a method for preventing disease in a subject caused by infection by a eukaryotic pathogen by administering to the subject a therapeutic amount of a modulator of an adenylyl cyclase of the eukaryotic pathogen.

The invention also provides a method for preventing disease in a subject caused by infection by a eukaryotic pathogen by administering to the subject a therapeutic amount of a modulator of a pathogen's adenylyl cyclase, wherein the amount of the modulator administered is effective at substantially preventing the pathogen from changing to a pathogenic state from a non-pathogenic state, or wherein the amount of modulator of the pathogen's adenylyl cyclase administered is effective to cause the pathogen to substantially revert to a non-pathogenic state from a pathogenic state. Preventing eukaryotic pathogens from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a method for preventing disease in a subject caused by infection by eukaryotic pathogen, by administering to the subject a therapeutic amount of a modulator of the pathogen's adenylyl cyclase, wherein the modulator of the pathogen's adenylyl cyclase inhibits the pathogen's adenylyl cyclase. In other embodiments, the modulator activates the pathogen's adenylyl cyclase.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase has a substantially biocidal effect upon the infecting pathogen. In other embodiments the modulator of the pathogen's adenylyl cyclase has a substantially biostatic effect upon the infecting pathogen. In certain embodiments, the amount of modulator of the pathogen's adenylyl cyclase does not substantially kill the infecting pathogen. In other embodiments, the amount of modulator of the pathogen's adenylyl cyclase does not inhibit or prevent the growth of the pathogen.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase affects more than one adenylyl cyclase of an infecting pathogen. The invention also provides that the modulator of the pathogen's adenylyl cyclase affects more than one adenylyl cyclase of more than one infecting pathogen.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase affects the response of the infecting pathogen's adenylyl cyclase to $CO_2$. In other embodiments, the modulator affects the response of the infecting pathogen's adenylyl cyclase to $HCO_3$. In other embodiments, the modulator affects the response of the infecting pathogen's adenylyl cyclase to pH.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase affects a Class III adenylyl cyclase.

The invention also provides a method for preventing disease in a subject caused by infection by a eukaryotic pathogen, by administering to the subject a therapeutic amount of a modulator of the pathogen's adenylyl cyclase, wherein the infection is caused by a pathogen that is resistant to one or more anti-microbial agents.

The invention also provides a method for preventing disease in a subject caused by infection by a eukaryotic pathogen, by administering to the subject a therapeutic amount of a modulator of the pathogen's adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for preventing disease in a subject caused by infection by a eukaryotic pathogen, by administering to the subject a therapeutic amount of a modulator of the pathogen's adenylyl cyclase, wherein the subject is a human.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase does not substantially inhibit the adenylyl cyclases of the subject. In this embodiment, the modulator of the pathogen's adenylyl cyclase is selective relative to subject's adenylyl cyclase(s). Preferably, the modulator of the pathogen's adenylyl cyclase is sufficiently selective against the subject's adenylyl cyclase that a therapeutic effect upon the infecting pathogen can be achieved without toxic regulation of the subject's adenylyl cyclase occurring.

The invention also provides a method for preventing infection by a eukaryotic pathogen in a subject, mediated by adenylyl cyclase of a pathogen in a subject, comprising modulating the adenylyl cyclase of the eukaryotic pathogen.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase is selected from the group consisting of small molecules, aptamers, and interfering RNA.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase is selected from the group consisting of one or more compounds selected from Table 1.

The invention also provides a method for preventing disease in a subject caused by infection by a eukaryotic pathogen, by administering to the subject a therapeutic amount of a modulator of the pathogen's adenylyl cyclase, wherein the modulator of the pathogen's adenylyl cyclase is selected from catechol estrogens and derivatives thereof.

The invention also provides a method for preventing disease in a subject caused by infection a eukaryotic pathogen, by administering to the subject a therapeutic amount of a modulator of the pathogen's adenylyl cyclase in combination with one or more additional therapeutic agents. In a further embodiment, the additional therapeutic agent is an anti-microbial agent.

In one aspect, the present invention features a method for preventing disease in a subject caused by infection by a fungus by administering to the subject a therapeutic amount of a modulator of a fungal adenylyl cyclase.

The invention also provides a method for preventing disease in a subject caused by infection by fungus by administering to the subject a therapeutic amount of a modulator of a fungal adenylyl cyclase, wherein the amount of the modulator administered is effective at substantially preventing the fungus from changing to a pathogenic state from a non-pathogenic state, or wherein the amount of modulator of the fungal adenylyl cyclase administered is effective to cause the fungus to substantially revert to a non-pathogenic state from a pathogenic state. Preventing a fungus from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a method for preventing disease in a subject caused by infection by a fungus, by administering to the subject a therapeutic amount of a modulator of a fungal adenylyl cyclase, wherein the modulator of the fungal adenylyl cyclase inhibits the fungal adenylyl cyclase. In other embodiments, the modulator activates the fungal adenylyl cyclase.

The invention also provides a method for preventing disease in a subject caused by infection by a fungus, by administering to the subject a therapeutic amount of a modulator of a fungal adenylyl cyclase, wherein the modulator of the fungal adenylyl cyclase has a substantially fungicidal effect upon the infecting fungus. In other embodiments the modulator of the pathogen's adenylyl cyclase has a substantially biostatic effect upon the infecting fungus. In certain embodiments, the amount of modulator of the fungal adenylyl cyclase does not substantially kill the infecting fungus. In other embodiments, the amount of modulator of the fungal adenylyl cyclase does not inhibit or prevent the growth of the fungus.

The invention also provides a method for preventing disease in a subject caused by infection by a fungus, by administering to the subject a therapeutic amount of a modulator of the fungal adenylyl cyclase, wherein the modulator of the fungal adenylyl cyclase affects more than one adenylyl cyclase of an infecting fungus. The invention also provides that the modulator of the fungal adenylyl cyclase affects more than one adenylyl cyclase of more than one infecting fungus.

The invention also provides a method for preventing disease in a subject caused by infection by a fungus, by administering to the subject a therapeutic amount of a modulator of a fungal adenylyl cyclase, wherein the modulator of fungal adenylyl cyclase affects the response of the fungal adenylyl cyclase to $CO_2$. In other embodiments, the modulator affects the response of the fungal adenylyl cyclase to $HCO_3$. In other embodiments, the modulator affects the response of the fungal adenylyl cyclase to pH.

The invention also provides a method for preventing disease in a subject caused by infection by a fungus, by administering to the subject a therapeutic amount of a modulator of fungal adenylyl cyclase, wherein the fungal adenylyl cyclase is a Class III adenylyl cyclase.

The invention also provides a method for preventing disease in a subject caused by infection by a fungus, by administering to the subject a therapeutic amount of a modulator of fungal adenylyl cyclase, wherein the infection is caused by a fungus that is resistant to one or more anti-fungal agents.

The invention also provides a method for preventing disease in a subject caused by infection by a fungus, by administering to the subject a therapeutic amount of a modulator of fungal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for preventing disease in a subject caused by infection by a fungus, by administering to the subject a therapeutic amount of a modulator of the fungal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for preventing disease in a subject caused by infection by a fungus, by administering to the subject a therapeutic amount of a modulator of fungal adenylyl cyclase, wherein the modulator of the fungal adenylyl cyclase does not substantially inhibit the adenylyl cyclases of the subject. In this embodiment, the modulator of the fungal adenylyl cyclase is selective relative to subject's adenylyl cyclase(s). Preferably, the modulator of the fungal adenylyl cyclase is sufficiently selective against the subject's adenylyl cyclase that a therapeutic effect upon the infecting fungus can be achieved without toxic regulation of the subject's adenylyl cyclase occurring.

The invention also provides a method of preventing infection by a fungus in a subject, mediated by fungal adenylyl cyclase in a subject, comprising modulating the adenylyl cyclase of the fungus.

The invention also provides a method for preventing disease in a subject caused by infection by a fungus, by administering to the subject a therapeutic amount of a modulator of fungal adenylyl cyclase, wherein the modulator of fungal adenylyl cyclase is selected from the group consisting of small molecules, aptamers, and interfering RNA.

The invention also provides a method for preventing disease in a subject caused by infection by a fungus, by administering to the subject a therapeutic amount of a modulator of fungal adenylyl cyclase, wherein the modulator of adenylyl cyclase is a quorum sensing molecule or a derivative of a quorum sensing molecule. In one embodiment, the quorum sensing molecule is farnesol or a derivative thereof. In another embodiment, the quorum sensing molecule is N-3-oxo-C12 homoserine lactone or a derivative thereof.

The invention also provides a method for preventing disease in a subject caused by infection by a fungus, by administering to the subject a therapeutic amount of a modulator of a fungal adenylyl cyclase, wherein the modulator of the fungal adenylyl cyclase is selected from catechol estrogens and derivatives thereof.

The invention also provides a method for preventing disease in a subject caused by infection by a fungus, by administering to the subject a therapeutic amount of a modulator of a fungal adenylyl cyclase, wherein the modulator of the fungal adenylyl cyclase is selected from the group consisting of one or more compounds selected from Table 1.

The invention also provides a method for preventing disease in a subject caused by infection by a fungus, by administering to the subject a therapeutic amount of a modulator of fungal adenylyl cyclase, wherein the amount of inhibitor of adenylyl cyclase administered is effective at substantially preventing the fungus from changing to a filamentous state from a non-filamentous state, or wherein the amount of inhibitor of adenylyl cyclase administered is effective to cause the fungus to substantially revert to a non-filamentous state from a filamentous state.

The invention also provides a method for preventing disease in a subject caused by infection by a fungus, by administering to the subject a therapeutic amount of a modulator of fungal adenylyl cyclase, wherein the infection is superficial, cutaneous, subcutaneous and/or systemic.

The invention also provides a method for preventing disease in a subject caused by infection by a fungus, by administering to the subject a therapeutic amount of a modulator of fungal adenylyl cyclase, wherein the fungus is selected from the group consisting of yeasts and moulds.

The invention also provides a method for preventing disease in a subject caused by infection by a fungus, by administering to the subject a therapeutic amount of a modulator of fungal adenylyl cyclase, wherein the fungus is from a genus selected from the group consisting of *Candida, Cryptococcus, Filobasidiella, Geotrichum, Issatchenkia, Malassezia, Pichia, Pneumocystis, Rhodotorula, Trichosporon, Absidia, Ajellomyces, Arthroderma, Aspergillus, Blastomyces, Cladophialophora, Coccidioides, Epidermophyton, Entomophthorales, Exophiala, Fonsecaea, Fusarium, Histoplasma, Hortaea, Madurella, Microsporum, Mucor, Nectria, Paecilomyces, Paracoccidioides, Penicillium, Pseudallescheria, Rhizopus, Scedosporium, Sporothrix*, and *Trichophyton*.

The invention also provides a method for preventing disease in a subject caused by infection by a fungus, by administering to the subject a therapeutic amount of a modulator of fungal adenylyl cyclase, wherein the fungus is selected from the group consisting of *Candida albicans, Candida glabrata, Candida guilliermondii, Candida krusei, Candida parapsilosis, Candida tropicalis, Cryptococcus neoformans, Filobasidiella neoformans, Geotrichum candidum, Issatchenkia orientalis, Malassezia furfur, Malassezia pachydermatis, Pichia anomala, Pichia guilliermondii, Pneumocystis carinii, Rhodotorula mucilaginosa, Trichosporon asahii, Trichosporon cutaneum, Trichosporon inkin, Trichosporon mucoides, Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigatus, Aspergillus niger, Blastomyces dermatitidis, Cladophialophora carrionii, Coccidioides immitis, Epidermophyton floccosum, Exophiala dermatitidis, Fonsecaea pedrosoi, Fusarium solani, Histoplasma capsulatum, Histoplasma duboisii, Hortaea werneckii, Madurella grisae, Microsporum canis, Microsporum fulvum, Microsporum gypseum, Mucor circinelloides, Nectria haematococca, Paecilomyces variotii, Paracoccidioides brasiliensis, Penicillium marneffei, Pseudallescheria boydii,*

*Rhizopus arrhizus, Rhizopus oryzae, Rhizomucor pusillus, Scedosporium apiospermum, Schizophyllum commune, Sporothrix schenckii, Trichophyton mentagrophytes, Trichophyton rubrum,* and *Trichophyton verrucosum.* In a preferred embodiment the invention also provides a method for preventing disease in a subject caused by infection by a fungus, by administering to the subject a therapeutic amount of a modulator of fungal adenylyl cyclase, wherein the fungus is selected from the group consisting of *Candida albicans, Candida glabrata, Cryptococcus neoformans, Aspergillus fumigatus, Coccidioides, Histoplasma, Blastomyces,* and *Paracoccidioides.*

The invention also provides a method for preventing disease in a subject caused by infection by a fungus, by administering to the subject a therapeutic amount of a modulator of fungal adenylyl cyclase in combination with one or more additional therapeutic agents. In a further embodiment, the additional therapeutic agent is an anti-fungal agent.

In one aspect, the present invention features a method for preventing disease in a subject caused by infection by a protozoan by administering to the subject a therapeutic amount of a modulator of a protozoal adenylyl cyclase.

The invention also provides a method for preventing disease in a subject caused by infection by a protozoan by administering to the subject a therapeutic amount of the modulator of a protozoal adenylyl cyclase, wherein the amount of the modulator administered is effective at substantially preventing the protozoan from changing to a pathogenic state from a non-pathogenic state, or wherein the amount of modulator of the protozoal adenylyl cyclase administered is effective to cause the protozoan to substantially revert to a non-pathogenic state from a pathogenic state. Preventing a protozoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, excystation, and changes in growth rate.

The invention also provides a method for preventing disease in a subject caused by infection by a protozoan, by administering to the subject a therapeutic amount of a modulator of a protozoal adenylyl cyclase, wherein the modulator of the protozoal adenylyl cyclase inhibits the protozoal adenylyl cyclase. In other embodiments, the modulator activates the protozoal adenylyl cyclase.

The invention also provides a method for preventing disease in a subject caused by infection by a protozoan, by administering to the subject a therapeutic amount of a modulator of a protozoal adenylyl cyclase, wherein the modulator of the protozoal adenylyl cyclase substantially kills the infecting protozoan. In other embodiments the modulator of the pathogen's adenylyl cyclase has a substantially biostatic effect upon the infecting protozoan. In certain embodiments, the amount of modulator of the protozoal adenylyl cyclase does not substantially kill the infecting protozoan. In other embodiments, the amount of modulator of the protozoal adenylyl cyclase does not inhibit or prevent the growth of the protozoan.

The invention also provides a method for preventing disease in a subject caused by infection by a protozoan, by administering to the subject a therapeutic amount of a modulator of the protozoal adenylyl cyclase, wherein the modulator of the protozoal adenylyl cyclase affects more than one adenylyl cyclase of an infecting protozoan. The invention also provides that the modulator of the protozoal adenylyl cyclase affects more than one adenylyl cyclase of more than one infecting protozoan.

The invention also provides a method for preventing disease in a subject caused by infection by a protozoan, by administering to the subject a therapeutic amount of a modulator of a protozoal adenylyl cyclase, wherein the modulator of protozoal adenylyl cyclase affects the response of the protozoal adenylyl cyclase to $CO_2$. In other embodiments, the modulator affects the response of the protozoal adenylyl cyclase to $HCO_3$. In other embodiments, the modulator affects the response of the protozoal adenylyl cyclase to pH.

The invention also provides a method for preventing disease in a subject caused by infection by a protozoan, by administering to the subject a therapeutic amount of a modulator of protozoal adenylyl cyclase, wherein the protozoal adenylyl cyclase is a Class III adenylyl cyclase.

The invention also provides a method for preventing disease in a subject caused by infection by a protozoan, by administering to the subject a therapeutic amount of a modulator of protozoal adenylyl cyclase, wherein the infection is caused by a protozoan that is resistant to one or more anti-protozoal agents.

The invention also provides a method for preventing disease in a subject caused by infection by a protozoan, by administering to the subject a therapeutic amount of a modulator of protozoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for preventing disease in a subject caused by infection by a protozoan, by administering to the subject a therapeutic amount of a modulator of the protozoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for preventing disease in a subject caused by infection by a protozoan, by administering to the subject a therapeutic amount of a modulator of protozoal adenylyl cyclase, wherein the modulator of the protozoal adenylyl cyclase does not substantially inhibit the adenylyl cyclases of the subject. In this embodiment, the modulator of the protozoal adenylyl cyclase is selective relative to subject's adenylyl cyclase(s). Preferably, the modulator of the protozoal adenylyl cyclase is sufficiently selective against the subject's adenylyl cyclase that a therapeutic effect upon the infecting protozoan can be achieved without toxic regulation of the subject's adenylyl cyclase occurring.

The invention also provides a method of preventing infection by a protozoan in a subject, mediated by protozoal adenylyl cyclase in a subject, comprising, modulating the adenylyl cyclase of the protozoan.

The invention also provides a method for preventing disease in a subject caused by infection by a protozoan, by administering to the subject a therapeutic amount of a modulator of protozoal adenylyl cyclase, wherein the modulator of protozoal adenylyl cyclase is selected from the group consisting of small molecules, aptamers, and interfering RNA.

The invention also provides a method for preventing disease in a subject caused by infection by a protozoan, by administering to the subject a therapeutic amount of a modulator of the protozoal adenylyl cyclase, wherein the modulator of the protozoal adenylyl cyclase is selected from catechol estrogens and derivatives thereof.

The invention also provides a method for preventing disease in a subject caused by infection by a protozoan, by administering to the subject a therapeutic amount of a modulator of a protozoal adenylyl cyclase, wherein the modulator of the protozoal adenylyl cyclase is selected from the group consisting of one or more compounds selected from Table 1.

The invention also provides a method for preventing disease in a subject caused by infection by a protozoan, by administering to the subject a therapeutic amount of a modulator of a protozoal adenylyl cyclase, wherein the protozoan is selected from the group consisting of Sarcodina, Ciliophora, Mastigophora, and Sporozoa.

The invention also provides a method for preventing disease in a subject caused by infection by a protozoan, by administering to the subject a therapeutic amount of a modulator of a protozoal adenylyl cyclase, wherein the protozoan is selected from the order gregarinia, coccidia, haemosporidia, and piroplasmida.

The invention also provides a method for preventing disease in a subject caused by infection by a protozoan, by administering to the subject a therapeutic amount of a modulator of a protozoal adenylyl cyclase, wherein the protozoan is selected from the group consisting of: *Acanthamoeba castellanii, Babesia bigemina, Babesia canis, Babesia divergens, Babesia microti, Balantidium coli, Besnoitia besnoiti, Cryptosporidium parvum, Cyclospora cayetensis, Eimeria acervulina, Eimeria bovis, Eimeria brunetti, Eimeria carpelli, Eimeria cyprinorum, Eimeria irresidua, Eimeria magna, Eimeria maxima, Eimeria mitis, Eimeria necatrix, Eimeria nieschulzi, Eimeria perforans, Eimeria phasiani, Eimeria praecox, Eimeria stiedae, Eimeria tenella, Eimeria truncata, Eimeria zurmii, Entamoeba histolytica, Giardia Lamblia, Leishmania donovani, Microsporidia, Naeglaria flowleri, Plasmodium falciparum, Plasmodium malariae, Plasmodium ovale, Plasmodium vivax, Pneumocystis carinii, Sarcocystis neurona, Sarcocystis tenella, Toxoplasma gondii, Trichomonas vaginalis, Trypanosoma brucei*, and *Trypanosoma cruzi*.

The invention also provides a method for preventing disease in a subject caused by infection by a protozoan, by administering to the subject a therapeutic amount of a modulator of protozoal adenylyl cyclase in combination with one or more additional therapeutic agents. In a further embodiment, the additional therapeutic agent is an anti-protozoal agent.

In one aspect, the present invention features a method for preventing disease in a subject caused by infection by a metazoan by administering to the subject a therapeutic amount of a modulator of a metazoal adenylyl cyclase.

The invention also provides a method for preventing disease in a subject caused by infection by a metazoan by administering to the subject a therapeutic amount of the modulator of a metazoal adenylyl cyclase, wherein the amount of the modulator administered is effective at substantially preventing the metazoan from changing to a pathogenic state from a non-pathogenic state, or wherein the amount of modulator of the metazoal adenylyl cyclase administered is effective to cause the metazoan to substantially revert to a non-pathogenic state from a pathogenic state. Preventing a metazoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a method for preventing disease in a subject caused by infection by a metazoan, by administering to the subject a therapeutic amount of a modulator of a metazoal adenylyl cyclase, wherein the modulator of the metazoal adenylyl cyclase inhibits the metazoal adenylyl cyclase. In other embodiments, the modulator activates the metazoal adenylyl cyclase.

The invention also provides a method for preventing disease in a subject caused by infection by a metazoan, by administering to the subject a therapeutic amount of a modulator of a metazoal adenylyl cyclase, wherein the modulator of the metazoal adenylyl cyclase substantially kills the infecting metazoan. In other embodiments the modulator of the pathogen's adenylyl cyclase has a substantially biostatic effect upon the infecting metazoan. In certain embodiments, the amount of modulator of the metazoal adenylyl cyclase does not substantially kill the infecting metazoan. In other embodiments, the amount of modulator of the metazoal adenylyl cyclase does not inhibit or prevent the growth of the metazoan.

The invention also provides a method for preventing disease in a subject caused by infection by a metazoan, by administering to the subject a therapeutic amount of a modulator of the metazoal adenylyl cyclase, wherein the modulator of the metazoal adenylyl cyclase affects more than one adenylyl cyclase of an infecting metazoan. The invention also provides that the modulator of the metazoal adenylyl cyclase affects more than one adenylyl cyclase of more than one infecting metazoan.

The invention also provides a method for preventing disease in a subject caused by infection by a metazoan, by administering to the subject a therapeutic amount of a modulator of a metazoal adenylyl cyclase, wherein the modulator of metazoal adenylyl cyclase affects the response of the metazoal adenylyl cyclase to $CO_2$. In other embodiments, the modulator affects the response of the metazoal adenylyl cyclase to $HCO_3$. In other embodiments, the modulator affects the response of the metazoal adenylyl cyclase to pH.

The invention also provides a method for preventing disease in a subject caused by infection by a metazoan, by administering to the subject a therapeutic amount of a modulator of metazoal adenylyl cyclase, wherein the metazoal adenylyl cyclase is a Class III adenylyl cyclase.

The invention also provides a method for preventing disease in a subject caused by infection by a metazoan, by administering to the subject a therapeutic amount of a modulator of a metazoal adenylyl cyclase, wherein the infection is caused by a metazoan that is resistant to one or more anti-metazoal agents.

The invention also provides a method for preventing disease in a subject caused by infection by a metazoan, by administering to the subject a therapeutic amount of a modulator of metazoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a method for preventing disease in a subject caused by infection by a metazoan, by administering to the subject a therapeutic amount of a modulator of the metazoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a method for preventing disease in a subject caused by infection by a metazoan, by administering to the subject a therapeutic amount of a modulator of metazoal adenylyl cyclase, wherein the modulator of the metazoal adenylyl cyclase does not substantially inhibit the adenylyl cyclases of the subject. In this embodiment, the modulator of the metazoal adenylyl cyclase is selective relative to subject's adenylyl cyclase(s). Preferably, the modulator of the metazoal adenylyl cyclase is sufficiently selective against the subject's adenylyl cyclase that a therapeutic effect upon the infecting metazoan can be achieved without toxic regulation of the subject's adenylyl cyclase occurring.

The invention also provides a method of preventing an infection by a metazoan in a subject, mediated by a metazoal adenylyl cyclase in a subject, comprising modulating the adenylyl cyclase of the metazoan.

The invention also provides a method for preventing disease in a subject caused by infection by a metazoan, by administering to the subject a therapeutic amount of a modulator of metazoal adenylyl cyclase, wherein the modulator of metazoal adenylyl cyclase is selected from the group consisting of small molecules, aptamers, and interfering RNA.

The invention also provides a method for preventing disease in a subject caused by infection by a metazoan, by administering to the subject a therapeutic amount of a modulator of the metazoal adenylyl cyclase, wherein the modulator of the metazoal adenylyl cyclase is selected from catechol estrogens and derivatives thereof.

The invention also provides a method for preventing disease in a subject caused by infection by a metazoan, by administering to the subject a therapeutic amount of a modulator of a metazoal adenylyl cyclase, wherein the modulator of the metazoal adenylyl cyclase is selected from the group consisting of one or more compounds selected from Table 1.

The invention also provides a method for preventing disease in a subject caused by infection by a metazoan, by administering to the subject a therapeutic amount of a modulator of a metazoal adenylyl cyclase, wherein the metazoan is selected from the group consisting of Cestodes, Trematodes, and Nematodes.

The invention also provides a method for preventing disease in a subject caused by infection by a metazoan, by administering to the subject a therapeutic amount of a modulator of a metazoal adenylyl cyclase, wherein the metazoan is selected from the group consisting of *Taenia solium, Taenia saginata, Diphyllobothrium latum, Echniococcus granulosus, Schistosomiasis, Clonorchis, Enterobius, Tichuris, Ascaris, Ancylostoma, Strongyloides, Trichinella, Anisakis, Wuchereria, Onchocerca, Loa, Dracuncululs,* and *Toxocara.*

The invention also provides a method for preventing disease in a subject caused by infection by a metazoan, by administering to the subject a therapeutic amount of a modulator of metazoal adenylyl cyclase in combination with one or more additional therapeutic agents. In a further embodiment, the additional therapeutic agent is an anti-metazoal agent.

In one aspect, the present invention features a pharmaceutical composition comprising a therapeutically effective amount of a modulator of an adenylyl cyclase of a eukaryotic pathogen.

The invention also provides a pharmaceutical composition comprising a therapeutically effective amount of a modulator of a eukaryotic pathogen's adenylyl cyclase, wherein the amount of the modulator administered is effective at substantially preventing the pathogen from changing to a pathogenic state from a non-pathogenic state, or wherein the amount of modulator of the pathogen's adenylyl cyclase administered is effective to cause the pathogen to substantially revert to a non-pathogenic state from a pathogenic state. Preventing eukaryotic pathogens from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a pharmaceutical composition comprising a therapeutically effective amount of a modulator of a eukaryotic pathogen's adenylyl cyclase, wherein the modulator of the pathogen's adenylyl cyclase inhibits the pathogen's adenylyl cyclase. In other embodiments, the modulator activates the pathogen's adenylyl cyclase.

The invention also provides a pharmaceutical composition comprising a therapeutically effective amount of a modulator of a eukaryotic pathogen's adenylyl cyclase, wherein the modulator of the pathogen's adenylyl cyclase has a substantially biocidal effect upon the infecting pathogen. In other embodiments the modulator of the pathogen's adenylyl cyclase has a substantially biostatic effect upon the infecting pathogen. In certain embodiments, the amount of modulator of the pathogen's adenylyl cyclase does not substantially kill the infecting pathogen. In other embodiments, the amount of modulator of the pathogen's adenylyl cyclase does not inhibit or prevent the growth of the pathogen.

The invention also provides a pharmaceutical composition comprising a therapeutically effective amount of a modulator of a eukaryotic pathogen's adenylyl cyclase, wherein the modulator of the pathogen's adenylyl cyclase affects more than one adenylyl cyclase of an infecting pathogen. The invention also provides that the modulator of the pathogen's adenylyl cyclase affects more than one adenylyl cyclase of more than one infecting pathogen.

The invention also provides a pharmaceutical composition comprising a therapeutically effective amount of a modulator of a eukaryotic pathogen's adenylyl cyclase, wherein the modulator of the pathogen's adenylyl cyclase affects the response of the infecting pathogen's adenylyl cyclase to $CO_2$. In other embodiments, the modulator affects the response of the infecting pathogen's adenylyl cyclase to $HCO_3$. In other embodiments, the modulator affects the response of the infecting pathogen's adenylyl cyclase to pH.

The invention also provides a pharmaceutical composition comprising a therapeutically effective amount of a modulator of a eukaryotic pathogen's adenylyl cyclase, wherein the modulator of the pathogen's adenylyl cyclase affects a Class III adenylyl cyclase.

The invention also provides a pharmaceutical composition comprising a therapeutically effective amount of a modulator of the pathogen's adenylyl cyclase, wherein the infection is caused by a pathogen that is resistant to one or more antimicrobial agents.

The invention also provides a pharmaceutical composition comprising a therapeutically effective amount of a modulator of a eukaryotic pathogen's adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a pharmaceutical composition comprising a therapeutically effective amount of a modulator of a eukaryotic pathogen's adenylyl cyclase, wherein the subject is a human.

The invention also provides a pharmaceutical composition comprising a therapeutically effective amount of a modulator of a eukaryotic pathogen's adenylyl cyclase, wherein the modulator of the pathogen's adenylyl cyclase does not substantially inhibit the adenylyl cyclases of the subject. In this embodiment, the modulator of the pathogen's adenylyl cyclase is selective relative to subject's adenylyl cyclase(s). Preferably, the modulator of the pathogen's adenylyl cyclase is sufficiently selective against the subject's adenylyl cyclase that a therapeutic effect upon the infecting pathogen can be achieved without toxic regulation of the subject's adenylyl cyclase occurring.

The invention also provides a pharmaceutical composition comprising a therapeutically effective amount of a modulator of a eukaryotic pathogen's adenylyl cyclase, wherein the modulator of the pathogen's adenylyl cyclase is selected from the group consisting of small molecules, aptamers, and interfering RNA.

The invention also provides a pharmaceutical composition comprising a therapeutically effective amount of a modulator of a eukaryotic pathogen's adenylyl cyclase, wherein the modulator of the pathogen's adenylyl cyclase is selected from the group consisting of one or more compounds selected from Table 1.

The invention also provides a pharmaceutical composition comprising a therapeutically effective amount of a modulator of a eukaryotic pathogen's adenylyl cyclase, wherein the modulator of the pathogen's adenylyl cyclase is selected from catechol estrogens and derivatives thereof.

The invention also provides a pharmaceutical composition comprising a therapeutically effective amount of a modulator of a eukaryotic pathogen's adenylyl cyclase in combination with one or more additional therapeutic agents. In a further embodiment, the additional therapeutic agent is an anti-microbial agent.

In one aspect, the present invention features a pharmaceutical composition comprising a therapeutically effective amount of a modulator of a fungal adenylyl cyclase.

The invention also provides a pharmaceutical composition comprising a therapeutically effective amount of a modulator of a fungal adenylyl cyclase, wherein the amount of the modulator administered is effective at substantially preventing the fungus from changing to a pathogenic state from a non-pathogenic state, or wherein the amount of modulator of the fungal adenylyl cyclase administered is effective to cause the fungus to substantially revert to a non-pathogenic state from a pathogenic state. Preventing a fungus from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a pharmaceutical composition comprising a therapeutically effective amount of a modulator of a fungal adenylyl cyclase, wherein the modulator of the fungal adenylyl cyclase inhibits the fungal adenylyl cyclase. In other embodiments, the modulator activates the fungal adenylyl cyclase.

The invention also provides a pharmaceutical composition comprising a therapeutically effective amount of a modulator of a fungal adenylyl cyclase, wherein the modulator of the fungal adenylyl cyclase has a substantially fungicidal effect upon the infecting fungus. In other embodiments the modulator of the pathogen's adenylyl cyclase has a substantially biostatic effect upon the infecting fungus. In certain embodiments, the amount of modulator of the fungal adenylyl cyclase does not substantially kill the infecting fungus. In other embodiments, the amount of modulator of the fungal adenylyl cyclase does not inhibit or prevent the growth of the fungus.

The invention also provides a pharmaceutical composition comprising a therapeutically effective amount of a modulator of the fungal adenylyl cyclase, wherein the modulator of the fungal adenylyl cyclase affects more than one adenylyl cyclase of an infecting fungus. The invention also provides that the modulator of the fungal adenylyl cyclase affects more than one adenylyl cyclase of more than one infecting fungus.

The invention also provides a pharmaceutical composition comprising a therapeutically effective amount of a modulator of a fungal adenylyl cyclase, wherein the modulator of fungal adenylyl cyclase affects the response of the fungal adenylyl cyclase to $CO_2$. In other embodiments, the modulator affects the response of the fungal adenylyl cyclase to $HCO_3$. In other embodiments, the modulator affects the response of the fungal adenylyl cyclase to pH.

The invention also provides a pharmaceutical composition comprising a therapeutically effective amount of a modulator of fungal adenylyl cyclase, wherein the fungal adenylyl cyclase is a Class III adenylyl cyclase.

The invention also provides a pharmaceutical composition comprising a therapeutically effective amount of a modulator of fungal adenylyl cyclase, wherein the infection is caused by a fungus that is resistant to one or more anti-fungal agents.

The invention also provides a pharmaceutical composition comprising a therapeutically effective amount of a modulator of fungal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a pharmaceutical composition comprising a therapeutically effective amount of a modulator of the fungal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a pharmaceutical composition comprising a therapeutically effective amount of a modulator of fungal adenylyl cyclase, wherein the modulator of the fungal adenylyl cyclase does not substantially inhibit the adenylyl cyclases of the subject. In this embodiment, the modulator of the fungal adenylyl cyclase is selective relative to subject's adenylyl cyclase(s). Preferably, the modulator of the fungal adenylyl cyclase is sufficiently selective against the subject's adenylyl cyclase that a therapeutic effect upon the infecting fungus can be achieved without toxic regulation of the subject's adenylyl cyclase occurring.

The invention also provides a pharmaceutical composition comprising a therapeutically effective amount of a modulator of fungal adenylyl cyclase, wherein the modulator of fungal adenylyl cyclase is selected from the group consisting of small molecules, aptamers, and interfering RNA.

The invention also provides a pharmaceutical composition comprising a therapeutically effective amount of a modulator of fungal adenylyl cyclase, wherein the modulator of adenylyl cyclase is a quorum sensing molecule or a derivative of a quorum sensing molecule. In one embodiment, the quorum sensing molecule is farnesol or a derivative thereof. In another embodiment, the quorum sensing molecule is N-3-oxo-C12 homoserine lactone or a derivative thereof.

The invention also provides a pharmaceutical composition comprising a therapeutically effective amount of a modulator of a fungal adenylyl cyclase, wherein the modulator of the fungal adenylyl cyclase is selected from catechol estrogens and derivatives thereof.

The invention also provides a pharmaceutical composition comprising a therapeutically effective amount of a modulator of a fungal adenylyl cyclase, wherein the modulator of the fungal adenylyl cyclase is selected from the group consisting of one or more compounds selected from Table 1.

The invention also provides a pharmaceutical composition comprising a therapeutically effective amount of a modulator of fungal adenylyl cyclase, wherein the amount of inhibitor of adenylyl cyclase administered is effective at substantially preventing the fungus from changing to a filamentous state from a non-filamentous state, or wherein the amount of inhibitor of adenylyl cyclase administered is effective to cause the fungus to substantially revert to a non-filamentous state from a filamentous state.

The invention also provides a pharmaceutical composition comprising a therapeutically effective amount of a modulator of fungal adenylyl cyclase, wherein the fungal infection to be treated is superficial, cutaneous, subcutaneous and/or systemic.

The invention also provides a pharmaceutical composition comprising a therapeutically effective amount of a modulator of fungal adenylyl cyclase, wherein the fungus is selected from the group consisting of yeasts and moulds.

The invention also provides a pharmaceutical composition comprising a therapeutically effective amount of a modulator of fungal adenylyl cyclase, wherein the fungus is from a genus selected from the group consisting of *Candida*, *Cryptococcus*, *Filobasidiella*, *Geotrichum*, *Issatchenkia*, *Malassezia*, *Pichia*, *Pneumocystis*, *Rhodotorula*, *Trichosporon*, *Absidia*, *Ajellomyces*, *Arthroderma*, *Aspergillus*, *Blastomyces*, *Cladophialophora*, *Coccidioides*, *Epidermophyton*, *Entomophthorales*, *Exophiala*, *Fonsecaea*, *Fusarium*, *Histoplasma*, *Hortaea*, *Madurella*, *Microsporum*, *Mucor*, *Nectria*, *Paecilomyces*, *Paracoccidioides*, *Penicillium*, *Pseudallescheria*, *Rhizopus*, *Scedosporium*, *Sporothrix*, and *Trichophyton*.

The invention also provides a pharmaceutical composition comprising a therapeutically effective amount of a modulator of fungal adenylyl cyclase, wherein the fungus is selected from the group consisting of *Candida albicans*, *Candida glabrata*, *Candida guilliermondii*, *Candida krusei*, *Candida parapsilosis*, *Candida tropicalis*, *Cryptococcus neoformans*, *Filobasidiella neoformans*, *Geotrichum candidum*, *Issatchenkia orientalis*, *Malassezia furfur*, *Malassezia pachydermatis*, *Pichia anomala*, *Pichia guilliermondii*, *Pneumocystis carinii*, *Rhodotorula mucilaginosa*, *Trichosporon asahii*, *Trichosporon cutaneum*, *Trichosporon inkin*, *Trichosporon mucoides*, *Absidia corymbifera*, *Ajellomyces capsulatus*, *Ajellomyces dermatitidis*, *Arthroderma benhamiae*, *Arthroderma fulvum*, *Arthroderma gypseum*, *Arthroderma incurvatum*, *Arthroderma otae*, *Arthroderma vanbreuseghemii*, *Aspergillus flavus*, *Aspergillus fumigatus*, *Aspergillus niger*, *Blastomyces dermatitidis*, *Cladophialophora carrionii*, *Coccidioides immitis*, *Epidermophyton floccosum*, *Exophiala dermatitidis*, *Fonsecaea pedrosoi*, *Fusarium solani*, *Histoplasma capsulatum*, *Histoplasma duboisii*, *Hortaea werneckii*, *Madurella grisae*, *Microsporum canis*, *Microsporum fulvum*, *Microsporum gypseum*, *Mucor circinelloides*, *Nectria haematococca*, *Paecilomyces variotii*, *Paracoccidioides brasiliensis*, *Penicillium marneffei*, *Pseudallescheria boydii*, *Rhizopus arrhizus*, *Rhizopus oryzae*, *Rhizomucor pusillus*, *Scedosporium apiospermum*, *Schizophyllum commune*, *Sporothrix schenckii*, *Trichophyton mentagrophytes*, *Trichophyton rubrum*, and *Trichophyton verrucosum*. In a preferred embodiment the invention also provides a pharmaceutical composition comprising a therapeutically effective amount of a modulator of fungal adenylyl cyclase, wherein the fungus is selected from the group consisting of *Candida albicans*, *Candida glabrata*, *Cryptococcus neoformans*, *Aspergillus fumigatus*, *Coccidioides*, *Histoplasma*, *Blastomyces*, and *Paracoccidioides*.

The invention also provides a pharmaceutical composition comprising a therapeutically effective amount of a modulator of fungal adenylyl cyclase in combination with one or more additional therapeutic agents. In a further embodiment, the additional therapeutic agent is an anti-fungal agent.

In one aspect, the present invention features a pharmaceutical composition comprising a therapeutically effective amount of a modulator of a protozoal adenylyl cyclase.

The invention also provides a pharmaceutical composition comprising a therapeutically effective amount of the modulator of a protozoal adenylyl cyclase, wherein the amount of the modulator administered is effective at substantially preventing the protozoan from changing to a pathogenic state from a non-pathogenic state, or wherein the amount of modulator of the protozoal adenylyl cyclase administered is effective to cause the protozoan to substantially revert to a non-pathogenic state from a pathogenic state. Preventing a protozoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, excystation, and changes in growth rate.

The invention also provides a pharmaceutical composition comprising a therapeutically effective amount of a modulator of a protozoal adenylyl cyclase, wherein the modulator of the protozoal adenylyl cyclase inhibits the protozoal adenylyl cyclase. In other embodiments, the modulator activates the protozoal adenylyl cyclase.

The invention also provides a pharmaceutical composition comprising a therapeutically effective amount of a modulator of a protozoal adenylyl cyclase, wherein the modulator of the protozoal adenylyl cyclase substantially kills the infecting protozoan. In other embodiments the modulator of the pathogen's adenylyl cyclase has a substantially biostatic effect upon the infecting protozoan. In certain embodiments, the amount of modulator of the protozoal adenylyl cyclase does not substantially kill the infecting protozoan. In other embodiments, the amount of modulator of the protozoal adenylyl cyclase does not inhibit or prevent the growth of the protozoan.

The invention also provides a pharmaceutical composition comprising a therapeutically effective amount of a modulator of the protozoal adenylyl cyclase, wherein the modulator of the protozoal adenylyl cyclase affects more than one adenylyl cyclase of an infecting protozoan. The invention also provides that the modulator of the protozoal adenylyl cyclase affects more than one adenylyl cyclase of more than one infecting protozoan.

The invention also provides a pharmaceutical composition comprising a therapeutically effective amount of a modulator of a protozoal adenylyl cyclase, wherein the modulator of protozoal adenylyl cyclase affects the response of the protozoal adenylyl cyclase to $CO_2$. In other embodiments, the modulator affects the response of the protozoal adenylyl cyclase to $HCO_3$. In other embodiments, the modulator affects the response of the protozoal adenylyl cyclase to pH.

The invention also provides a pharmaceutical composition comprising a therapeutically effective amount of a modulator of protozoal adenylyl cyclase, wherein the protozoal adenylyl cyclase is a Class III adenylyl cyclase.

The invention also provides a pharmaceutical composition comprising a therapeutically effective amount of a modulator of protozoal adenylyl cyclase, wherein the infection is caused by a protozoan that is resistant to one or more anti-protozoal agents.

The invention also provides a pharmaceutical composition comprising a therapeutically effective amount of a modulator of protozoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a pharmaceutical composition comprising a therapeutically effective amount of a modulator of the protozoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a pharmaceutical composition comprising a therapeutically effective amount of a modulator of protozoal adenylyl cyclase, wherein the modulator of the protozoal adenylyl cyclase does not substantially inhibit the adenylyl cyclases of the subject. In this embodiment, the modulator of the protozoal adenylyl cyclase is selective relative to subject's adenylyl cyclase(s). Preferably, the modulator of the protozoal adenylyl cyclase is sufficiently selective against the subject's adenylyl cyclase that a therapeutic effect upon the infecting protozoan can be achieved without toxic regulation of the subject's adenylyl cyclase occurring.

The invention also provides a pharmaceutical composition comprising a therapeutically effective amount of a modulator of protozoal adenylyl cyclase, wherein the modulator of protozoal adenylyl cyclase is selected from the group consisting of small molecules, aptamers, and interfering RNA.

The invention also provides a pharmaceutical composition comprising a therapeutically effective amount of a modulator of the protozoal adenylyl cyclase, wherein the modulator of the protozoal adenylyl cyclase is selected from catechol estrogens and derivatives thereof.

The invention also provides a pharmaceutical composition comprising a therapeutically effective amount of a modulator of a protozoal adenylyl cyclase, wherein the modulator of the protozoal adenylyl cyclase is selected from the group consisting of one or more compounds selected from Table 1.

The invention also provides a pharmaceutical composition comprising a therapeutically effective amount of a modulator of a protozoal adenylyl cyclase, wherein the protozoan is selected from the group consisting of Sarcodina, Ciliophora, Mastigophora, and Sporozoa.

The invention also provides a pharmaceutical composition comprising a therapeutically effective amount of a modulator of a protozoal adenylyl cyclase, wherein the protozoan is selected from the order: gregarinia, coccidia, haemosporidia, and piroplasmida.

The invention also provides a pharmaceutical composition comprising a therapeutically effective amount of a modulator of a protozoal adenylyl cyclase, wherein the protozoan is selected from the group consisting of: *Acanthamoeba castellanii, Babesia bigemina, Babesia canis, Babesia divergens, Babesia microti, Balantidium coli, Besnoitia besnoiti, Cryptosporidium parvum, Cyclospora cayetensis, Eimeria acervulina, Eimeria bovis, Eimeria brunetti, Eimeria carpelli, Eimeria cyprinorum, Eimeria irresidua, Eimeria magna, Eimeria maxima, Eimeria mitis, Eimeria necatrix, Eimeria nieschulzi, Eimeria perforans, Eimeria phasiani, Eimeria praecox, Eimeria stiedae, Eimeria tenella, Eimeria truncata, Eimeria zurmii, Entamoeba histolytica, Giardia Lamblia, Leishmania donovani, Microsporidia, Naeglaria flowleri, Plasmodium falciparum, Plasmodium malariae, Plasmodium ovale, Plasmodium vivax, Pneumocystis carinii, Sarcocystis neurona, Sarcocystis tenella, Toxoplasma gondii, Trichomonas vaginalis, Trypanosoma brucei*, and *Trypanosoma cruzi.*

The invention also provides a pharmaceutical composition comprising a therapeutically effective amount of a modulator of protozoal adenylyl cyclase in combination with one or more additional therapeutic agents. In a further embodiment, the additional therapeutic agent is an anti-protozoal agent.

In one aspect, the present invention features a pharmaceutical composition comprising a therapeutically effective amount of a modulator of a metazoal adenylyl cyclase.

The invention also provides a pharmaceutical composition comprising a therapeutically effective amount of the modulator of a metazoal adenylyl cyclase, wherein the amount of the modulator administered is effective at substantially preventing the metazoan from changing to a pathogenic state from a non-pathogenic state, or wherein the amount of modulator of the metazoal adenylyl cyclase administered is effective to cause the metazoan to substantially revert to a non-pathogenic state from a pathogenic state. Preventing a metazoan from entering a pathogenic state involves preventing the expression of genes and/or the production of proteins that are associated with pathogenesis, and preventing changes associated with the pathogenic state such as morphological changes, changes in shape, toxin production, expression of virulence factors, germination, formation of biofilm, and changes in growth rate.

The invention also provides a pharmaceutical composition comprising a therapeutically effective amount of a modulator of a metazoal adenylyl cyclase, wherein the modulator of the metazoal adenylyl cyclase inhibits the metazoal adenylyl cyclase. In other embodiments, the modulator activates the metazoal adenylyl cyclase.

The invention also provides a pharmaceutical composition comprising a therapeutically effective amount of a modulator of a metazoal adenylyl cyclase, wherein the modulator of the metazoal adenylyl cyclase substantially kills the infecting metazoan. In other embodiments the modulator of the pathogen's adenylyl cyclase has a substantially biostatic effect upon the infecting metazoan. In certain embodiments, the amount of modulator of the metazoal adenylyl cyclase does not substantially kill the infecting metazoan. In other embodiments, the amount of modulator of the metazoal adenylyl cyclase does not inhibit or prevent the growth of the metazoan.

The invention also provides a pharmaceutical composition comprising a therapeutically effective amount of a modulator of the metazoal adenylyl cyclase, wherein the modulator of the metazoal adenylyl cyclase affects more than one adenylyl cyclase of an infecting metazoan. The invention also provides that the modulator of the metazoal adenylyl cyclase affects more than one adenylyl cyclase of more than one infecting metazoan.

The invention also provides a pharmaceutical composition comprising a therapeutically effective amount of a modulator of a metazoal adenylyl cyclase, wherein the modulator of metazoal adenylyl cyclase affects the response of the metazoal adenylyl cyclase to $CO_2$. In other embodiments, the modulator affects the response of the metazoal adenylyl cyclase to $HCO_3$. In other embodiments, the modulator affects the response of the metazoal adenylyl cyclase to pH.

The invention also provides a pharmaceutical composition comprising a therapeutically effective amount of a modulator of metazoal adenylyl cyclase, wherein the metazoal adenylyl cyclase is a Class III adenylyl cyclase.

The invention also provides a pharmaceutical composition comprising a therapeutically effective amount of a modulator of a metazoal adenylyl cyclase, wherein the infection is caused by a metazoan that is resistant to one or more anti-metazoal agents.

The invention also provides a pharmaceutical composition comprising a therapeutically effective amount of a modulator of metazoal adenylyl cyclase, wherein the subject is a eukaryote. In further embodiments the subject is a plant, an animal, a bird, a fish, or a mammal. The subject may also be livestock such as, cattle, swine, sheep, poultry, and horses, or pets, such as dogs and cats.

The invention also provides a pharmaceutical composition comprising a therapeutically effective amount of a modulator of the metazoal adenylyl cyclase, wherein the subject is a human. In another embodiment, the human is immune-compromised. For example, the immune compromised human may be infected with HIV, undergoing chemotherapy, affected by a blood cancer, a transplant recipient, receiving immunosuppressant medication, receiving opioid medication, or a burn victim.

The invention also provides a pharmaceutical composition comprising a therapeutically effective amount of a modulator of metazoal adenylyl cyclase, wherein the modulator of the metazoal adenylyl cyclase does not substantially inhibit the adenylyl cyclases of the subject. In this embodiment, the modulator of the metazoal adenylyl cyclase is selective relative to subject's adenylyl cyclase(s). Preferably, the modulator of the metazoal adenylyl cyclase is sufficiently selective against the subject's adenylyl cyclase that a therapeutic effect upon the infecting metazoan can be achieved without toxic regulation of the subject's adenylyl cyclase occurring.

The invention also provides a pharmaceutical composition comprising a therapeutically effective amount of a modulator of metazoal adenylyl cyclase, wherein the modulator of metazoal adenylyl cyclase is selected from the group consisting of small molecules, aptamers, and interfering RNA.

The invention also provides a pharmaceutical composition comprising a therapeutically effective amount of a modulator of the metazoal adenylyl cyclase, wherein the modulator of the metazoal adenylyl cyclase is selected from catechol estrogens and derivatives thereof.

The invention also provides a pharmaceutical composition comprising a therapeutically effective amount of a modulator of a metazoal adenylyl cyclase, wherein the modulator of the metazoal adenylyl cyclase is selected from the group consisting of one or more compounds selected from Table 1.

The invention also provides a pharmaceutical composition comprising a therapeutically effective amount of a modulator of a metazoal adenylyl cyclase, wherein the metazoan is selected from the group consisting of: Taenia solium, Taenia saginata, Diphyllobothrium latum, Echniococcus granulosus, Schistosomiasis, Clonorchis, Enterobius, Tichuris, Ascaris, Ancylostoma, Strongyloides, Trichinella, Anisakis, Wuchereria, Onchocerca, Loa, Dracuncululs, and Toxocara.

The invention also provides a pharmaceutical composition comprising a therapeutically effective amount of a modulator of metazoal adenylyl cyclase in combination with one or more additional therapeutic agents. In a further embodiment, the additional therapeutic agent is an anti-metazoal agent.

The invention also provides a method for controlling the growth of a eukaryotic pathogen in vitro comprising contacting the eukaryotic pathogen with a modulator of the eukaryotic pathogen's adenylyl cyclase. In one embodiment, the invention also provides a method for controlling the growth of a fungi in vitro comprising contacting the fungi with a modulator of fungal adenylyl cyclase. In another embodiment, the invention also provides a method for controlling the growth of a protozoan in vitro comprising contacting the protozoan with a modulator of protozoal adenylyl cyclase. In another embodiment, the invention also provides a method for controlling the growth of a metazoan in vitro comprising contacting the metazoan with a modulator of metazoal adenylyl cyclase.

The invention also provides a method of identifying a selective modulator of a eukaryotic pathogen's adenylyl cyclase, the method comprising: testing the modulator against one or more human adenylyl cyclases, testing the modulator against the eukaryotic pathogen's adenylyl cyclase, and determining the relative selectivity of the modulator for the said adenylyl cyclases. In one embodiment, the pathogen is a fungus. In one embodiment, the pathogen is a protozoan. In one embodiment, the pathogen is a metazoan.

The invention also provides a method for facilitating the growth of a eukaryotic organism in vitro comprising contacting the organism with an activator of adenylyl cyclase. In one embodiment, the organism is a fungus. In one embodiment, the organism is a protozoan. In one embodiment, the organism is a metazoan.

The invention also provides a method for the preparation of a fungal metabolite, comprising fermentation of a fungus in a fermentation medium comprising a modulator of fungal adenylyl cyclase, and isolating the fungal metabolite from the fermentation medium. In a further embodiment the fungal metabolite is an enzyme. In another embodiment the fungal metabolite is an antibiotic. In one embodiment the fungal metabolite is produced by a fungus selected from the group consisting of Aspergillus citricus, As. niger, As. nidulans, As. oryzae, Aspergillus flavus, As. citricus, As. awamori, As. terreus, A. alliaceus, A. atroviolaceus, A. candidus, A. carbonarius, A. carneus, A. clavatus, A. ficuum, A. fumigatus, A. giganteus, A. itaconicus, A. kiliense, A. melleus, A. ochraceus, A. parasiticus, A. phoenicis, A. rugulosus, A. saitoi, A. soyae, A. tamarii, A. wentii, Au. pullulans, Acremonium persicinum, Acremonium chrysogenum, Calcarisporium arbuscula, Chaetomium gracile, Cryphonectria parasitica, Eupenicillium javanicum, F. coccophilum, Fusarium solani, Fusarium oxysporum, G. candidum, Mortiella ramannianua, Mortierella vinaceae, Mu. Circinelloides, N. crassa, Nectria lucida, Penicillium vitale, Penicillum decumbens, Penicillium aurantiogriseum, Pe. chrysogenum, P. amagasakiense, P. baculatum, P. citrinum, P. dupontii, P. funiculosum, P. griseofulvum, P. griseoroseum, P. isariiforme, P. italicum, P. jensenii, P. lilacium, P. luteum, P. pinophilum, P. roqueforti, P. simplicissimum, P. turbatum, P. vermiculatum, R. arrhizus, Rhizopus oryzae, Rhizop. stolonifer, R. niveus, Rhizomucor miechei, R. pusillus, R. microsporus, R. meihei, Sclerotinia libertiana, T. longibrachiatum, T. reesei, Trichoderma viride, Tolypocladium geodes, T. inflatum, and Trichoderma polysporum. In one embodiment the modulator of fungal adenylyl cyclase is effective at causing the fungus to be in a substantially filamentous state. In one embodiment the modulator of fungal adenylyl cyclase is effective at causing the fungus to be in a substantially non-filamentous state. In one embodiment the fungal adenylyl cyclase is $CO_2/HCO_3/pH$ sensitive.

DETAILED DESCRIPTION OF THE INVENTION

Figure 1:
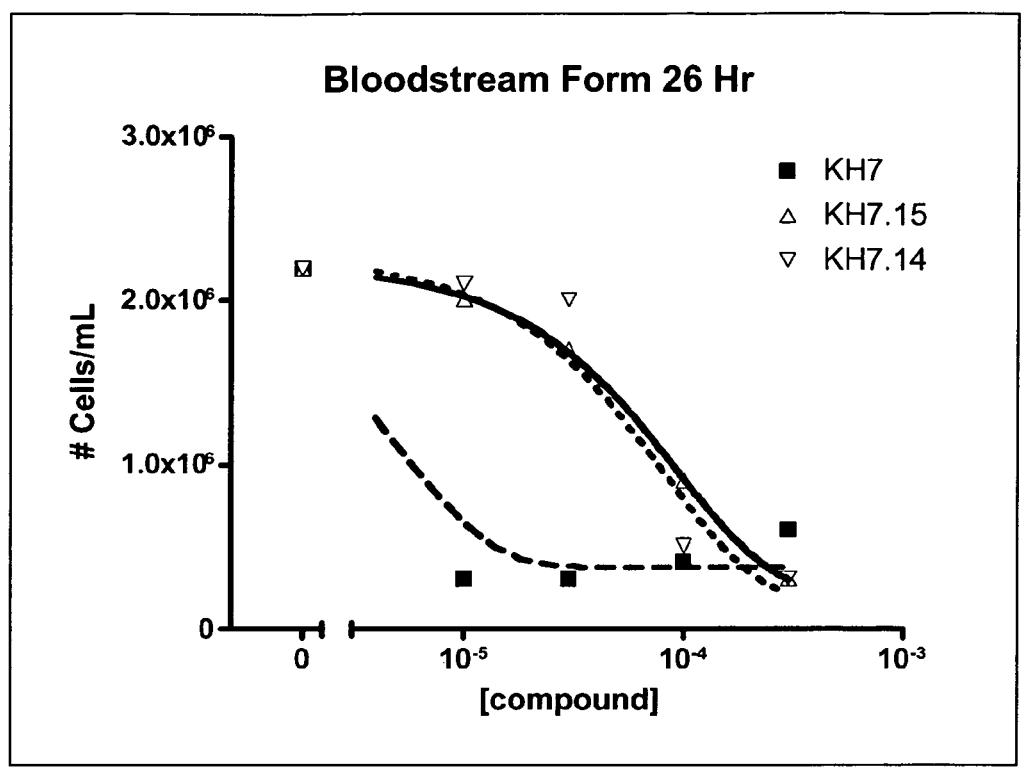
FIG. 1. The effect of compounds KH7, KH7.14, and KH7.15 on the growth of the bloodstream form (trypomastigotes) of *Trypansoma brucei*. Cell density (cells/mL) as measured by using a Coulter counter is plotted against the molar concentration of the compound.

The invention provides a method for preventing or treating a disease by administering an effective amount of a modulator of eukaryotic adenylyl cyclase.

Adenylyl cyclase is a group of enzymes that catalyze the conversion of ATP to cAMP and pyrophosphate. Six classes of adenylyl cyclase enzymes have been identified based upon protein sequence and properties. Class I adenylyl cyclases are found primarily in enteric bacteria. Class II adenylyl cyclases include the toxins secreted by pathogens such as edema factor (EF) from *Bacillus anthracis* (which causes anthrax), CyaA from *Bordetella pertussis* (the cause of whooping cough), and ExoY from *Pseudomonas aeruginosa* (the cause of various nosocomial infections). Class III is the largest known group and consists of cyclases found in bacteria, archaea and eukaryotes. The class IV enzymes are found in archaeal organisms, and also in some bacteria including the plague-causing *Yersinia pestis*. Class V is comprised of one adenylyl cyclase from the strict anaerobic bacterium *Prevotella ruminicola*. Class VI is found in the nitrogen fixing bacteria *Rhizobium etli*. All six classes of enzymes are present in bacteria, while only enzymes belonging to class III have been described in eukaryotes.

In mammalian cells cAMP is produced by two related families of the class III adenylyl cyclase, transmembrane adenylyl cyclases (tmAC) and soluble adenylyl cyclases (sAC). These two families differ in sub-cellular localization and respond to different regulators. The primary regulators for tmACs are hetrotrimeric G proteins, which transmit extracellular signals via G protein-coupled receptors. In contrast, sACs are regulated by intracellular bicarbonate and calcium.

Carbon dioxide ($CO_2$) is the end product of metabolism in animals. In all physiological systems, $CO_2$ exists in an almost instantaneous equilibrium with bicarbonate and pH($H^+$ concentration) due to the presence of the enzyme, carbonic anhydrase, which catalyzes the rapid interconversion of carbon dioxide and water into carbonic acid, which dissociates into protons and bicarbonate ions according to the following equation:

$$CO_2 + H_2O \leftrightarrows H_2CO_3 \leftrightarrows HCO_3^- + H^+$$

This reaction occurs spontaneously in aqueous solution, but does so slowly. The enzyme carbonic anhydrase greatly increases the rate of the reaction.

During pathogenesis in a host, an infecting organism is challenged to respond to a diverse and dynamic set of environmental conditions. A variety of pathogenic organisms have evolved to exploit the dramatic environmental shifts encountered once inside an infectible host as a signal to alter their growth and virulence properties. One such environmental signal that infectious bacteria exploit is the change in concentration of $CO_2$, $HCO_3^-$, and/or pH. There is a 150-fold difference in $CO_2$ concentration inside the human (or animal) body (5% $CO_2$) compared to the atmosphere (0.03% $CO_2$). Because $CO_2$ levels are in equilibrium with the concentration of bicarbonate and pH levels, these infectious organisms may sense differences in concentrations of $CO_2$, $HCO_3$, or pH levels to detect when they are inside an infectible host.

$CO_2$/$HCO_3$ regulated cyclase is the evolutionarily defined target in fungal pathogens for preventing pathogenic conversion. We demonstrated that the *Candida* and *Cryptococcus* adenylyl cyclase (AC) are $CO_2$/$HCO_3$ sensitive, and when they are inhibited by small molecules (the pan sAC-like AC inhibitor, KH7), the morphological transition essential for pathogenesis is blocked. In support of our findings, the mechanism which fungi has evolved to regulate their own pathogenesis is via inhibition of the fungal AC. Our recent data identify the fungal AC as the target that *Candida albicans* itself uses to autoregulate its own transition. Pathogenesis is autoregulated by a fungal synthesized and secreted factor which functions as a 'quorum sensor.' Additionally, commensally growing bacteria also target the fungal AC to limit pathogenesis in the shared niche.

$CO_2$/$HCO_3$ regulated adenylyl cyclase is the $CO_2$ chemosensor in parasitic protozoa which permits growth inside infectible hosts. We have demonstrated using specific, small molecule inhibitors and activators, that the $CO_2$/$HCO_3$ regulated cyclase in *Plasmodium* is essential for growth inside red blood cells, and it is solely responsible for the observed experimental dependence upon $CO_2$ for in vitro culturing. In addition, our work has identified a lead compound selective for killing malaria parasites growing in red blood cells (see WO 2005/070419, incorporated herein by reference in its entirety).

Other eukaryotic pathogens utilize $CO_2$/$HCO_3$/pH-sensing ACs to regulate pathogenicity. Adenylyl cyclases have genetically been shown to be important for the expression of virulence factors in other infectious protozoa, including *Trypanosoma brucei*, *Trypanosoma cruzi*, and *Leishmania donovani*. In *Trypanosomes* and *Leishmania*, virulence factors are only expressed when the protozoa infect a host, i.e., when they are exposed to the high $CO_2$ environment inside their human hosts, and evolutionarily, the ACs in these organisms are predicted to be $CO_2$/$HCO_3$/pH-sensing. Unlike in the protozoa that causes malaria, the $CO_2$/$HCO_3$/pH-sensing ACs in the Trypanosomes and *Leishmania* appear to be essential, not for growth, but for inducing a developmental differentiation that converts an innocuous commensal into a pathogenic organism (similar to the case for fungi). In these cases, the inhibitor would be an effective therapeutic agent by preventing expression or secretion of a toxin, and activators would be useful for mimicking growth conditions inside an infectible host.

Eukaryotic Pathogens

Pathogens are organisms that cause disease in another organism. Typically, pathogens are organisms such as bacteria, viruses, fungi, or parasites such as worms. In each case, the infecting organism uses the host body to live and grow. Eukaryotic pathogens include members of the kingdoms Fungi, Protista, and Metazoa.

Fungal Pathogens

Fungi cause a wide variety of diseases in humans including aspergillosis, blastomycosis, candidiasis, coccidiodomycosis, cryptococcosis, histoplasmosis, paracoccidiomycosis, sporotrichosis, and zygomycosis. Other diseases caused by fungal infection include chromoblastomycosis, otomycosis, phaeohyphomycosis, rhinosporidiosis, and dermatomycoese. Fungal infections (mycoses) may be classified as superficial, growing only on the surface of the skin or hair, cutaneous in which fungal growth occurs in the outer layers of the skin, nails or hair (i.e., athlete's foot and ringworm), subcutaneous infections that penetrate below the skin and involve subcutaneous tissues, connective tissue and bone, and systemic infections in which the fungus infects internal organs often becoming disseminated throughout the body.

Aspergillosis is a large spectrum of diseases caused by members of the genus *Aspergillus*. The three principal manifestations are allergic bronchopulmonary aspergillosis, pulmonary aspergilloma and invasive aspergillosis. Colonization of the respiratory tract is also common. The clinical manifestation and severity of the disease typically depends upon the immunologic state of the patient. Lowered host resistance due to such factors as underlying debilitating disease, neutropenia, chemotherapy, disruption of normal flora, and the use of antimicrobial agents and steroids can predispose the patient to colonization and/or invasive disease. *Aspergillus* species are frequently secondary opportunistic pathogens in patients with bronchiectasis, carcinoma, other mycoses, sarcoid, and tuberculosis. The organism can infect the lungs, inner ear, sinuses and, rarely, the eye of previously healthy persons.

Blastomycosis is caused by the endemic dimorphic fungi *Blastomyces dermatitidis*. The fungus grows in soil as a mould producing conidia. The infection is acquired by inhalation of the conidia, which transform into the yeast form once in the lungs, and is capable of causing an acute pulmonary disease similar bacterial pneumonia. Most cases of blastomycosis becomes manifest during a chronic phase that may affect the lungs, the skin, the bones, the genitourinary tract and other organs.

The various forms of candidiasis are among the most frequent fungal infections in humans. *Candida* species can produce infections in otherwise healthy individuals and in individuals with reduced immune system function. *Candida* species can both colonize (be present without causing disease) or infect any body surface. Invasive candidiasis, also called systemic candidiasis, is a complicated collection of diseases. These forms of candidiasis are only seen in individuals with reduced function of the immune system or some other type of weakening of their defenses and may involve any organ of the body.

Coccidioidomycosis an infection caused by the dimorphic fungus *Coccidioides immitis*. The disease is endemic only in regions of the Western Hemisphere. Outbreaks occur following dust storms, earthquakes, and earth excavation when spores (arthroconidia) are dispersed. Coccidioidomycosis is acquired from inhalation of the spores. Once in the lungs, the arthroconidia transform into spherical cells called "spherules". An acute respiratory infection occurs 7 to 21 days after exposure and typically resolves rapidly. However, the infection may alternatively result in a chronic pulmonary condition or disseminate to the meninges, bones, joints, and subcutaneous and cutaneous tissues.

Cryptococcosis refers to the infections produced by the encapsulated yeast *Cryptococcus neoformans*. The infection commonly starts following inhalation of the organism. The primary infection may remain localized in the lungs or may disseminate throughout the body. Primary pulmonary infections are usually asymptomatic. However, a chronic form may develop producing a variety of lesions. Once disseminated, meningitis is a common manifestation. Cryptococcosis is considered an opportunistic infection which mainly affects immuno-compromised individuals, but may affect healthy individuals as well.

Histoplasmosis describes two groups of disease. The more common use of this term refers to the forms of histoplasmosis caused by *Histoplasma capsulatum* var *capsulatum* (also called *Histoplasma capsulatum*). This organism most often causes pulmonary disease, although disseminated forms also occur. The other group of histoplasmosis is caused by *Histoplasma capsulatum* var. *duboisii* (also known as *Histoplasma duboisii*), which most often causes skin and bone disease.

Paracoccidioidomycosis refers to disease produced by *Paracoccidioides brasiliensis*. Inhalation of conidia is presumably the route of acquisition. Primary infection is generally asymptomatic. The fungus can remain dormant for years within lymph nodes to appear later, probably in relation to some form of immunodeficiency. Interestingly, paracoccidiodomycosis affects primarily men and people older than 30. A juvenile form with a poor prognosis occurs rarely. The adult form usually manifests with painful ulcerated lesions in the mouth. Other clinical presentations include cutaneous lesions, lymphadenopathy, dysphagia, and hoarseness. Finally a clinical picture identical to pulmonary tuberculosis (fever, weight loss, and productive cough with blood-tinged sputum) may also occur.

Sporotrichosis refers to the infection caused by the dimorphic fungus *Sporothrix schenckii*. Sporotrichosis is acquired through direct inoculation into the skin and rarely via inhalation of conidia. As a consequence, the majority of cases are localized lesions affecting the skin and subcutaneous tissues with minimal if any systemic manifestation. The most common form of extracutaneous sporotrichosis is osteoarthritis. Pulmonary and disseminated forms of disease are seen, and these typically affect immunosuppressed individuals.

Zygomycosis refers to the angiotropic (blood vessel-invading) infection produced by the various Zygomycetes. The most common species causing disease are *Absidia corymbifera, Rhizomucor pusillus*, and *Rhizopus arrhizus*.

Murormycosis is caused by members of the family Mucorales (and sometimes the family Entomophthorales) and are generally acute and rapidly developing in debilitated patients. The disease is associated with acidotic diabetics, malnourished children, and severely burned patients. It is also occurs in patients with leukemia, lymphoma, and AIDS, and in patients using immunosuppressive therapy such as corticosteroids. The fungi penetrate the respiratory or intestinal mucosa and may enter through breaks in the skin as well. Localized lesions may develop, followed by spreading to the blood and subsequently to other organs. These infections are often fatal.

Chromoblastomycosis is a chronic localized infection of the skin and subcutaneous tissue caused by many different fungi. The lesions are verrucoid, ulcerated, and crusted, and may be flat or raised 1-3 cm. Satellite lesions may develop by lymphatic spread to adjacent areas. The mycosis usually remains localized with extensive keloid formation. However, some of the causative agents (e.g., *Fonsecaea pedrosoi* and *Phialophora verrucosa*) may disseminate to the brain.

Other fungal diseases include *pneumocystis*, an infection of the lung caused by *Pneumocystis carinii*. This organism is a common cause of fatal pneumonia in AIDS patients.

The invention provides a methods and pharmaceutical compositions for preventing and treating disease in a subject caused by infection by a fungus, by administering to the subject a therapeutic amount of a modulator of fungal adenylyl cyclase, wherein the fungus is from a genus selected from the group consisting of *Candida, Cryptococcus, Filobasidiella, Geotrichum, Issatchenkia, Malassezia, Pichia, Pneumocystis, Rhodotorula, Trichosporon, Absidia, Ajellomyces, Arthroderma, Aspergillus, Blastomyces, Cladophialophora, Coccidioides, Epidermophyton, Entomophthorales, Exophiala, Fonsecaea, Fusarium, Histoplasma, Hortaea, Madurella, Microsporum, Mucor, Nectria, Paecilomyces,*

*Paracoccidioides, Penicillium, Pseudallescheria, Rhizopus, Scedosporium, Sporothrix*, and *Trichophyton*.

The invention provides methods and pharmaceutical compositions for preventing and treating disease in a subject caused by infection by a fungus, by administering to the subject a therapeutic amount of a modulator of fungal adenylyl cyclase, wherein the fungus is selected from the group consisting of *Candida albicans, Candida glabrata, Candida guilliermondii, Candida krusei, Candida parapsilosis, Candida tropicalis, Cryptococcus neoformans, Filobasidiella neoformans, Geotrichum candidum, Issatchenkia orientalis, Malassezia furfur, Malassezia pachydermatis, Pichia anomala, Pichia guilliermondii, Pneumocystis carinii, Rhodotorula mucilaginosa, Trichosporon asahii, Trichosporon cutaneum, Trichosporon inkin, Trichosporon mucoides, Absidia colymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigatus, Aspergillus niger, Blastomyces dermatitidis, Cladophialophora carrionii, Coccidioides immitis, Epidermophyton floccosum, Exophiala dermatitidis, Fonsecaea pedrosoi, Fusarium solani, Histoplasma capsulatum, Histoplasma duboisii, Hortaea werneckii, Madurella grisae, Microsporum canis, Microsporum fulvum, Microsporum gypseum, Mucor circinelloides, Nectria haematococca, Paecilomyces variotii, Paracoccidioides brasiliensis, Penicillium marneffei, Phialophora verrucosa, Pseudallescheria boydii, Rhizopus arrhizus, Rhizopus oryzae, Rhizomucor pusillus, Scedosporium apiospermum, Schizophyllum commune, Sporothrix schenckii, Trichophyton mentagrophytes, Trichophyton* rubrum, and *Trichophyton verrucosum*.

Protazoa

Protozoa, the animal-like Protists, are mostly single-celled, motile protists that feed by phagocytosis, though there are numerous exceptions. Protozoa are ubiquitous throughout aqueous environments and the soil, commonly surviving dry periods as cysts or spores. Protozoa generally exist in two basic forms: the active, growing form called the "trophozoite;" and the dormant, resistant form called the cyst (although some disease causing protozoa have much more complicated life cycles). The trophozoite form proliferates in tissues, causing damage that results in clinical disease. The cyst is able to survive in an external environment and is usually the form that is transmitted from host to host.

Some protozoa go through an intermediate stage in blood-sucking insects. For example, *Trypanosoma brucei*, which causes African Trypanosomiasis (African Sleeping Sickness) and Nagana in cattle. *T. brucei* has a complex life cycle, with transmission to a mammalian host occurring through the bite of a Tse Tse fly vector. As an infected Tse Tse fly takes a blood meal, it injects metacyclic trypomastigotes into the host bloodstream. In the host bloodstream, metacyclic trypomastigotes transform into bloodstream trypomastigotes, and these proliferate in host bodily fluids (blood, lymph, and spinal fluid), avoiding immune system attack through an antigen switching mechanism. Tse Tse flies taking blood meals from infected hosts ingest the bloodstream trypomastigotes. Within the gut of the Tse Tse fly, bloodstream trypomastigotes differentiate into procyclic trypomastigotes. Ultimately procyclic trypomastigotes differentiate into metacyclic trypomastigotes in the insect salivary gland, completing the life cycle.

Based on the method of locomotion, many protozoa are grouped into 4 groups; sarcodina, ciliophora, mastigophora, and sporozoa.

Sarcodina, commonly known as amoebas, move by extending a section of their cytoplasm (a pseudopodium). They are usually found in marine and fresh water. *Entamoeba histolytica* causes the disease amebiasis. *E. histolytica* and has been associated with chronic fatigue syndrome.

Ciliophora, or Ciliates, move by using the multiple cilia. *Balantidium coli* can infect the human intestinal tract, where it can invade and destroy the intestinal lining. Its normal habitat is the intestinal tract of hogs, but it can also be found in marine and fresh water worldwide, causing the disease known as balantidiasis.

Mastigophora (Flagellates) is a subphylum of protozoa that has one or more flagella. Members of this group cause the diseases richomoniasis, giardiasis, trypanosomiasis, and leishmaniasis.

Sporozoa (typically non-motile) is a class of parasitic protozoa that include *Plasmodium* and *Toxoplasma*, responsible for malaria and toxoplasmosis, respectively. They have both a sexual and asexual phase. They mainly target the epithelial cells of the intestinal tract, but can also be found in the liver and other organs.

The invention provides methods and pharmaceutical compositions for preventing and treating disease in a subject with a disease caused by infection by a protozoan, by administering to the subject a therapeutic amount of a modulator of a protozoal adenylyl cyclase, wherein the protozoan is selected from the order gregarinia, coccidia, haemosporidia, and piroplasmida.

The invention provides methods and pharmaceutical compositions for preventing and treating disease in a subject with a disease caused by infection by a protozoan, by administering to the subject a therapeutic amount of a modulator of a protozoal adenylyl cyclase, wherein the protozoan is selected from the group consisting of: *Acanthamoeba castellanii, Babesia bigemina, Babesia canis, Babesia divergens, Babesia microti, Balantidium coli, Besnoitia besnoiti, Cryptosporidium parvum, Cyclospora cayetensis, Eimeria acervulina, Eimeria bovis, Eimeria brunetti, Eimeria carpelli, Eimeria cyprinorum, Eimeria irresidua, Eimeria magna, Eimeria maxima, Eimeria mitis, Eimeria necatrix, Eimeria nieschulzi, Eimeria perforans, Eimeria phasiani, Eimeria praecox, Eimeria stiedae, Eimeria tenella, Eimeria truncata, Eimeria zurmii, Entamoeba histolytica, Giardia Lamblia, Leishmania donovani, Microsporidia, Naeglaria flowleri, Plasmodium falciparum, Plasmodium malariae, Plasmodium ovale, Plasmodium vivax, Pneumocystis carinii, Sarcocystis neurona, Sarcocystis tenella, Toxoplasma gondii, Trichomonas vaginalis, Trypanosoma brucei*, and *Trypanosoma cruzi*.

Metazoa

Metazoan pathogens include Cestodes, Trematodes and Nematodes. Cestoda is a class within the phylum Platyhelminthes and includes parasitic flatworms, called cestodes or tapeworms, that live in the digestive tract of vertebrates as adults and often in the bodies of various animals as juveniles. Tapeworms of the order Cyclophyllidea (the cyclophyllid cestodes) are among the most important cestode parasites of humans and domesticated animals. The cyclophyllid cestodes include *Dipylidium caninum*, which is carried by fleas and infect pets such as dogs and cats and pet their human owners, *Hymenolepis nana*, which infects mammals including humans and is carried by beetles, *Hymenolepis diminuta*, which infects mammals using insects as intermediate hosts, and the pork tapeworm, *Taenia solium*, and the beef tapeworms, *T. saginata*. Other Cestodes that cause disease include *Diphyllobothrium latum*, which is the longest tapeworm in humans, and *Echniococcus granulosis*, which causes hydatid cyst disease.

Trematoda (Trematodes) is a class within the phylum Platyhelminthes. Trematodes are parasitic flatworms, commonly referred to as flukes. The flukes can be classified into two groups, on the basis of the system which they infect. Tissue flukes are species which infect the bile ducts, lungs, or other tissues. This group includes the lung fluke, *Paragonimus westermani*, and the liver flukes, *Clonorchis sinensis* and *Fasciola hepatica*. The other group are known as blood flukes and inhabit the blood in some stage of their life cycle. Blood flukes include various species of the genus *Schistosoma*, which cause schistosomiasis.

Nematodes are roundworms that contain a great many parasitic forms, including pathogens in most plants and animals. Nematodes that are parasitic on humans include whipworms (Tichuris), hookworms (Ancylostoma and *Necator*), pinworms (Enterobius), threadworms (Strongyloides), ascarids, and filarids. Other Nematode pathogens include *Wuchereria, Onhocerca, Loa, Dracunculus* (Guinea worm), and *Toxocara*. The species *Trichinella spiralis*, commonly known as the trichina worm, occurs in rats, pigs, and humans, and is responsible for the disease trichinosis. *Baylisascaris* usually infests wild animals but can be deadly to humans as well. *Haemonchus contortus* is one of the most abundant infectious agents in sheep.

One aspect of the present invention is the prevention or treatment of infection by a eukaryotic pathogen by preventing the infecting pathogen from entering the pathogenic state, or by causing the infecting pathogen to revert from a pathogenic state to a non-pathogenic state. A pathogenic state includes any state upon entering the host that confers an advantage to the pathogen or otherwise contributes to the infection, including the expression of genes and/or the production of proteins that are associated with pathogenesis, and changes associated with the pathogenic state such as changing shape or morphology, formation of hyphae, increase or decrease in growth rate, germination, excystation, release of toxins, expression of virulence factors, capsule formation, and formation of biofilm. The pathogenic state also includes expression of genes associated with pathogenesis, such as genes that provide a mechanism to avoid the host immune system, scavenge nutrients, alter motility, damage host tissues, and spread through host cells, tissues, and organs.

Preventing the infecting eukaryotic pathogen from entering a pathogenic state, or causing the pathogen to revert to a non-pathogenic state, can create beneficial effects in preventing and treating infection by the pathogen including reducing or preventing symptoms of infection, and increasing susceptibility of the invading pathogen to the host's immune system, slowing the pathogen's growth, preventing sporulation, preventing the production of toxins, preventing the expression of virulence factors, and causing the pathogen to react in manner inconsistent with the host environment and adversely effecting its ability to infect the host.

In certain embodiments the adenylyl cyclase of the eukaryotic pathogen is $pH/HCO_3/CO_2$ sensitive. The adenylyl cyclase of the eukaryotic pathogen may be a soluble adenylyl cyclase (sAC) or may have substantial homology to sAC.

Modulation of a eukaryotic pathogen's adenylyl cyclase includes inhibition of the cyclase activity or activation of the cyclase activity. Inhibition of the adenylyl cyclase will reduce cellular levels of cAMP, while activation of the adenylyl cyclase will increase cellular cAMP levels.

The modulator of a eukaryotic pathogen's adenylyl cyclase may have a biocidal or biostatic effects. Biostatic refers to an effect that substantially restricts the ability of the pathogen to grow, whereas a biocidal treatment is substantially lethal to the pathogen. However, it is not necessary for the modulator to kill the pathogen to be effective.

In one embodiment, the invention features a method of inhibiting adenylyl cyclase of a eukaryotic pathogen, the method comprising contacting eukaryotic cells with a compound that inhibits adenylyl cyclase of the eukaryotic pathogen.

In one embodiment, the invention features a method of treating an infection by a eukaryotic pathogen, mediated by adenylyl cyclase of a pathogen in a subject, comprising, modulating the adenylyl cyclase of the pathogen.

For the treatment of a subject, it is preferred that the modulator of the eukaryotic pathogen's adenylyl cyclase does not substantially inhibit or activate an adenylyl cyclase (or guanylyl cyclase) of the subject. Modulators that are sufficiently selective against the subject's adenylyl cyclase help ensure that a therapeutic effect upon the infecting pathogen can be achieved without adverse regulation of subject's adenylyl cyclase(s).

The term "subject" as used herein refers to any organism in need of treatment, or requiring preventative therapy to prevent infection, with the methods and compositions of the invention. The subject may be a plant or an animal. The subject animal includes fish, birds, or mammals. The subject may be livestock, such as cattle, swine, sheep, poultry, and horses, or pets, such as dogs and cats. The subject may also be a human.

The methods and pharmaceutical compositions of the present invention may also be used to treat or prevent infection in at-risk subjects, for example preventing or treating infection in a subject following surgery.

A human subject may be otherwise healthy or may have a condition that makes the human particularly susceptible to infection by a pathogen. For example, the human may be immune compromised due to infection with HIV, due to the effects of chemotherapy, due to affliction with a blood cancer, due to immunosuppressant medication, or due to opioid medication. The human may also be a transplant recipient or a burn victim.

The modulator of a eukaryotic pathogen's adenylyl cyclase may include, but is not limited to, small molecules, aptamers, small interfering RNA.

In one aspect of the invention, the modulator of a eukaryotic pathogen's adenylyl cyclase may be an aptamer, which are oligonucleic acid or polypeptide molecules that bind a specific target molecule. They can be synthesized specifically or selected from a pool using various screening methods known in the art for example a yeast two-hybrid system.

In one aspect of the invention, the modulator of a eukaryotic pathogen's adenylyl cyclase may be a small molecule. In this context, the term small molecule refers to small organic compounds, such as heterocycles, peptides, saccharides, steroids, and the like. The small molecule modulators preferably have a molecular weight of less than about 1500 Daltons, and more preferably less than about 500 Daltons. The compounds may be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The small molecule modulators of a eukaryotic pathogen's adenylyl cyclase include but are not limited to small molecules that may interact with the cyclase ATP binding domain, $CO_2/HCO_3^-/$pH sensing domain, or other regulatory protein binding site. Small molecule libraries can be screened for inhibitory activity using high-throughput biochemical, enzymatic, or cell based assays. The assays can be formulated to detect the ability of a test compound to inhibit or activate the formation of cAMP from ATP.

In certain embodiments the small molecule modulator of a eukaryotic pathogen's adenylyl cyclase may be selected from catechol estrogens and derivatives thereof. Catechol estrogens are steroid metabolites that elicit physiological responses through binding to a variety of cellular targets. Catechol estrogens may directly inhibit soluble adenylyl cyclases and trans-membrane adenylyl cyclases. Derivatives of catechol estrogens include compounds in which functional groups on the estrogen nucleus have been modified, for example through reduction or oxidation, or a metabolite of catechol estrogens. The catechol estrogens may be further derivatized, for example, as the esters, ethers, oximes, hydrazones, hydroxyamines, carbamate esters, alkoxyesters, carbonate esters, or PEG derivatives.

In other embodiments of the invention, the small molecule modulator is selected from the compounds disclosed in WO 2005/070419, incorporated herein by reference in its entirety. In other embodiments, the modulator of eukaryotic pathogen's adenylyl cyclase is selected from compounds listed in Table 1, and combinations thereof.

The present invention also provides a method for the prevention or treatment of
a disease caused by infection by a eukaryotic pathogen in a subject, by administering to the subject a composition comprising a therapeutically effective amount of a modulator of the eukaryotic pathogen's adenylyl cyclase and a pharmaceutically acceptable excipient.

In another aspect, the present invention provides pharmaceutically acceptable compositions which comprise a therapeutically-effective amount of one or more of the modulators of a eukaryotic pathogen's adenylyl cyclase, as described above, formulated together with one or more pharmaceutically acceptable excipients. The active ingredient and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

A therapeutically effective amount of the pharmaceutical composition of the present invention is sufficient to treat or prevent disease caused by infection by a eukaryotic pathogen. The therapeutically effective amount may prevent the infecting pathogen from changing to a pathogenic state, substantially inhibit disease causing factors associated with the pathogenic state, and/or cause the pathogen to revert from a pathogenic state to a non-pathogenic state. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, $19^{th}$ Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the modulator of a eukaryotic pathogen's adenylyl cyclase and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

The composition of the present invention may be administered alone or may be administered in combination with one or more of other therapeutic agents, such as antibiotics. Antibiotics may include, but are not limited to, macrolides (eryrthromycin, azithromaycin, clarithromycin, etc.), β-lactams (penems, cephems, carbapenems and carbacephems, such as penicillin, amoxicillin, ticarcillin, cefazolin, cefaclor, cefepime, ceftriaxone, loracarbef, imipenem, etc.), aminoglycosides (gentamycin, tobramycin, etc.), glycopeptides (vancomycin, etc.), quinolones (ciprofloxacin, levofloxacin, ofloxacin, etc.), tetracyclines (tetracycline, doxycycline, etc.), oxazolidinones (linezolid, etc.), lincosamides (clindamycin, etc.), and chloramphenicol.

The composition of the present invention may be administered in combination with one or more antifunal agents. Such antifungal agents may include, but are not limited to, allylamines and other non-azole ergosterol biosynthesis inhibitors (amorolfine, butenafine, naftifine, terbinafine, etc.); antimetabolites (flucytosine, etc.); azoles (fluconazole, itraconazole, ketoconazole, posaconazole, voriconazole, clotrimazole, econazole, miconazole, oxiconazole, sulconazole, terconazole, tioconazole, etc.); glucan synthesis inhibitors (caspofungin, etc.); and polyenes (amphotericin B, nystatin, pimaricin, etc.).

The composition of the present invention may be administered in combination with one or more antiparasitic agents including, but not limited to diloxanide, eflornithine, furazolidone, ivermectin, levamisole, melarsoprol, mepacrine, metronidazole, ornidazole, paromomycin, pentamidine, piperazine, pyrimethamine, stibogluconate, sulfadoxine, and timidazole.

In a combination therapy, the modulator of a eukaryotic pathogen's adenylyl cyclase may be administered before, during, or after commencing therapy with another agent (such as an antibiotic agent), as well as any combination thereof, i.e., before and during, before and after, during and after, or before, during and after commencing the additional therapy.

In one embodiment of the invention, the modulator of a eukaryotic pathogen's adenylyl cyclase may be added to animal feed, for the prevention and/or treatment of disease in livestock and pets. This may be accomplished by preparing an appropriate feed premix containing the modulator of the eukaryotic pathogen's adenylyl cyclase in an effective amount and incorporating the premix into the complete ration. Alternatively, an intermediate concentrate or feed supplement containing the active ingredient can be blended into the feed. The way in which such feed premixes and complete rations can be prepared and administered are described in references (such as "Applied Animal Nutrition", W.H. Freedman and CO., San Francisco, U.S.A., 1969 or "Livestock Feeds and Feeding" O and B books, Corvallis, Ore., U.S.A., 1977).

Another aspect of the present invention is a method for inducing the pathogenic state in vitro. By exposing a eukaryotic pathogen to one or more activators of adenylyl cyclase, changes associated with the pathogenic state can be induced in vitro, including, increased growth rate, growth in various conditions such as increased $CO_2$ levels, morphological changes, and expression of genes and proteins associated with the pathogenic state. In addition, induction of the pathogenic state may then be followed by testing candidate compounds for their ability to inhibit the pathogenic state or aspects of the pathogenic state.

Model systems for the analysis of effects on the ability of a pathogen to switch to, or maintain, a pathogenic state may be in vitro systems or in vivo systems. For example, two forms of *T. brucei* can be cultured in vitro, bloodstream trypomastigotes and procyclic trypomastigotes. Both in vivo and in vitro, high cell density in bloodstream form cells triggers differentiation from a long slender form to a short stumpy form. This differentiation, thought to be controlled by an unidentified quorum sensing factor, termed Stumpy Inducing Factor (SIF), leads to cell cycle arrest via the cAMP pathway (Vassella et al. *J. Cell Science*. 1997. November; 110 (Pt 21) pp. 2661-71.). Therefore, the cAMP pathway regulates progression through the cell cycle and may serve as a good candidate for controlling *T. brucei* infections.

For decades, the laboratory mouse has provided an alternative platform for infectious disease research where the pathogen under study is intractable to routine laboratory manipulation. For example, four species of rodent malaria (*Plasmodium yoelii, Plasmodium berghei, Plasmodium chabaudi* and *Plasmodium vinckei*) isolated from wild thicket rats in Africa have been adapted to grow in laboratory rodents (Carter, R. & Diggs, C. L. *Parasitic Protozoa*. pp. 359-465. Academic Press, New York/San Francisco/London, 1977).

In vivo and in vitro models for metazoan pathogens are also known in the art. For example, In the study of Cestode worms, Hymenolepis species and Mesocestoides species have been extensively studied because their life cycle stages can be easily cultured in vitro, and can also be conveniently maintained in laboratory animal hosts (for a review of Cestode models see Siles-Lucas, M. & Hemphill, A., *Adv Parasitology*. 2002. Vol. 51, pp. 133-230.).

Identifying modulators of a eukaryotic pathogen's adenylyl cyclase can be accomplished by assays that detect adenylyl cyclase activity. Detecting adenylyl cyclase activity can be accomplished in a number of ways including measuring the formation of cAMP, and measuring the conversion of ATP to cAMP. These techniques are well known in the art and commercially available kits containing detailed protocols are also an option. For example, commercial kits include the cAMP Chemiluminescent immunoassay Assay Kit, cAMP-Screen Direct™ from Applied Biosystems, cAMP Radiometric FlashPlate® ($^{125}$I) Assay Kit from PerkinElmer, the cAMP Enzyme Immunoassay Assay Kit from Sigma-Aldrich, the CatchPoint cAMP Assay Kit from Molecular Devices, and the cAMP Colorimetric Assay Kit from Calbiochem, to name a few. Many commercially available kits are intended for or adaptable to high throughput screening for adenylyl cyclase activity.

The concentration of cAMP in samples can be measured by a receptor binding assay (Nordstedt, C. and Fredholm, B B. Anal Biochem Vol 189, pp. 231-234. 1990). This method utilizes competition for binding to a cAMP binding protein (for example the regulatory subunit of mammalian protein kinase A or the CRP protein of *E. coli*) between cAMP present in the sample or standard and radiolabeled cAMP. Many different methods can be used to separate bound from free cAMP (e.g. filtration, precipitation, etc.). The amount of radiolabeled cAMP bound to the cAMP binding protein can be measured in a scintillation counter.

Another method for measuring cAMP concentration in cell extracts is by radioimmunoassay, which utilizes a cAMP-specific antibody (Steiner et al. *PNAS. Vol.* 64, pp. 367-373. 1969). A modification of this procedure utilizes a specific antibody generated against 2'-O-monosuccinyl adenosine 3',5'-cyclic monophosphate for detection of femtomolar amounts of cAMP (Harper et al. *Journal of Cyclic Nucleotide Research*. Vol. 1, pp. 207-218. 1975). By converting cAMP to an acetylated derivative that binds the antibody with higher affinity, sensitivity of these assays is enhanced. In this radioimmunoassay, a radiolabeled cAMP competes with the cAMP in the sample or standard for binding to the cAMP-specific antibody. Bound, radiolabeled cAMP is isolated and measured with a scintillation counter. Although more sensitive than the aforementioned radioreceptor method, immunoassays often require more sample manipulation, which may increase variability and assay time.

Measurements of adenylyl cyclase activity can also involve quantifying the conversion of ATP to cAMP. One method utilizes a [$^{32}$P]-labeled ATP, which is converted by the adenylyl cyclase to [$^{32}$P]cAMP. Another method involves incubating cells with [$^3$H]adenine to label intracellular pools of ATP. The [$^3$H]ATP is converted to [$^3$H]cAMP by adenylyl cyclase. Thus accumulation of [$^3$H]cAMP is used as measure of adenylyl cyclase activity. Both of these methods require the separation of radioactively labeled cAMP from other components of the reaction mixture, which is often accomplished by sequential chromatography on Dowex cation-exchange and alumina columns (Solomon et al. *Analytical Biochemistry*. Vol. 58, pp. 541-548. 1974). Another approach that can be utilized for determining adenylyl cyclase activity involves using an anti-cAMP antibody (described above) to assess cAMP formation following the incubation of cell lysates with ATP. This approach avoids the use of radioactive substrate and can also be used for assessing cAMP accumulation in intact cells. An important consideration of this assay is that only a small fraction of the ATP substrate is converted to cAMP. Thus, there is the potential that components of the reaction mixture may interfere with the antibody-cAMP interaction. For this reason, it is necessary to confirm that the buffers used for cAMP generation do not interfere with the detection of cAMP in a solution containing a known cAMP concentration.

It is important to note that adenylyl cyclase activity can be influenced by several factors depending upon the type of adenylyl cyclase (transmembrane or soluble) and the organism from which it is derived. The adenylyl cyclase activity is dependent on the presence of divalent cations, and/or dependent on the presence of other molecules such as bicarbonate, which must be present during the incubation. Also, when measuring mammalian transmembrane adenylyl cyclase, which is regulated by hormones via G-protein-coupled receptors, GTP (or a nonhydrolyzable GTP analog) should be included in the incubations. In addition, degradation of ATP by enzymes (nucleotidases and hydrolases) present in cell lysates can result in depletion of the substrate. To prevent this problem, incubations may be performed in the presence of an ATP regeneration system consisting of creatinine phosphate and creatinine phosphokinase (or phospho(enol)pyruvate and pyruvate kinase). Finally, phosphodiesterases present in cell lysates can hydrolyze cAMP to AMP. Therefore, incubations typically contain one or more phosphodiesterase inhibitors to prevent cAMP breakdown.

The conversion of ATP to cAMP in an adenylyl cyclase assay can also be determined by an immunoassay. In this assay, the antigen, cAMP, is bound to an antibody, then a second, labeled antibody is bound to the antigen-antibody complex. The amount of bound, labeled antibody is then measured. This method has several advantages relative to the conversion assay described above because it does not require the use of large amounts of $^{32}P$ and the cAMP does not need to be isolated by column chromatography.

To determine the modulating activity of a compound, these assays may be performed on whole cells or cell lysates. To determine the inhibitory effects of compounds on a eukaryotic pathogen's adenylyl cyclase activity, the pathogen can be grown in conditions that elevate cAMP levels via the cyclase of interest such as elevated $CO_2$, $HCO_3^-$ or lower pH levels, with and without the compounds of interest, and analyzed for reduced cAMP levels. To determine activation of a eukaryotic pathogen's cyclases the pathogen may be grown in the presence of the compounds of interest and analyzed for increased cAMP levels. To determine inhibitory activity against human (or other subject) adenylyl cyclases, appropriate cells in culture may be grown in stimulatory conditions that increase cAMP levels. For example, stimulators of sAC include high glucose (in beta cells), neurotrophins and/or netrin (in neurons), TNF (in neutrophils), while for tmACs, stimulators include forskolin, or any of a large number of Gs-coupled hormones. The compound of interest, and assayed for reduced cAMP levels. Alternatively, inhibitory activity may be examined by observing reduction in basal levels of cyclase activity.

To determine stimulatory activity against human (or other subject) adenylyl cyclases, appropriate cells in culture may be grown in the presence of the compound and increases in cAMP levels monitored.

Alternatively assays examining modulators of adenylyl cyclase may be performed using purified adenylyl cyclase preparations in combination with the compound to be tested. The adenylyl cyclase to be studied can be purified by a number of ways that are known in the art for example immunoprecepitation, column chromatography with antibodies, and purification of heterologously expressed fusion proteins such as polyhistidine tagged (His-tagged) adenylyl cyclase. Polyhistidine-tags are often used for affinity purification of polyhistidine-tagged recombinant proteins that are expressed in $E.$ $coli$ or other prokaryotic expression systems. The bacterial cells are harvested by centrifugation and the resulting cell pellet can be lysed with detergents or enzymes such as lysozyme. The raw lysate is passed through a column containing immobilized nickel ions, which binds the polyhistidine tag attached to the adenylyl cyclase. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The purity and amount of protein can be assessed by SDS-PAGE and western blotting.

Adenylyl cyclase proteins may also by purified using immunoaffinity chromatography. The procedure involves immobilizing an antibody that specifically binds the adenylyl cyclase to a column material. A cell lysate is passed through the column, which selectively binds the protein. The protein can be eluted by changing the pH or the salt concentration.

The activity of heterologously expressed and purified pathogen sAC is determined by assaying in the presence of bicarbonate, $MgCl_2$ and ATP. To determine selectivity of the compound for the infecting pathogen's sAC, a counter screen with purified human (or other host) sAC protein can be performed. A further counter screen using a whole cell lysate stimulated with forskolin—which would reflect the activities of tmACs can also be performed.

The selectivity of a compound for a eukaryotic pathogen's adenylyl cyclase is determined by comparing the effects of the compound on the pathogen's cAMP production to the effects of the compound on the subject's cAMP production. For example, a compound that is highly selective for inhibiting a eukaryotic pathogen's adenylyl cyclase will substantially prevent that pathogen's cyclase from generating cAMP under conditions where the cyclase would, in the absence of the compound, catalyze the formation of cAMP. Further, the selective compound will not substantially inhibit or stimulate an adenylyl cyclase from the subject.

One aspect of the invention provides a method of identifying a selective modulator of a eukaryotic pathogen's adenylyl cyclase. Selectivity of the modulator of a eukaryotic pathogen's adenylyl cyclase may be determined by measuring the inhibitory or stimulatory effect on the pathogen's adenylyl cyclase and by also measuring the effect on adenylyl cyclase of the intended subject. Highly selective modulators will affect the activity of the pathogen's adenylyl cyclase but will have little or no effect on the activity of the adenylyl cyclase from the intended subject.

The efficacy and potential side effects of modulators of a eukaryotic pathogen's adenylyl cyclase may be tested in animal models. Effects of infection on tissues can be examined by fixing the tissue, embedding in paraffin, and cutting sections for staining followed by microscopy.

Detailed descriptions of conventional methods, discussed herein such as those employed in the analysis of proteins, gene expression, light microscopy, bacterial culture, mammalian cell culture, and the like can be obtained from numerous publications such as Molecular Cloning: A Laboratory Manual (Cold Spring Harbor Laboratory Press. 1989), Current Protocols in Microbiology (Wiley InterScience), Current Protocols in Cell Biology (Wiley InterScience), and Current Protocols in Molecular Biology (Wiley InterScience). All references mentioned herein are incorporated by reference in their entirety.

EXAMPLES

Example 1

Effect of KH7 Compounds on Human Adenylyl Cyclase

Compounds were selected from the Chem Div library based on their chemical structure. These compounds were assayed to determine their effects on the activity of human soluble and transmembrane adenylyl cyclases.

In Vitro Analysis

Purified human sAC protein was used in an in vitro adenylyl cyclase assay. Purification of the protein is described in detail in Litvin et al. 2003. (J. Biol. Chem. 278:15922-15926.). This paper also describes the general conditions for a sAC cyclase assay. The specific conditions for the in vitro assay are as follows.

For basal sAC activity, an assay master mixture with sufficient volume for all reactions was prepared containing:
  50 mM Tris (pH 7.5)
  20 mM Creatine phosphate
  100 U/ml creatine phosphokinase (CPK)
  1 mM DTT
  10 mM $MgCl_2$ An aliquot of the master mixture was added to the purified human sAC. The assay mixture also included the indicated concentration of KH compound, or an equivalent volume of vehicle (i.e., DMSO) as control. The reaction was started by adding 5 mM ATP (total assay volume=100 μL). The reaction mixture was incubated at 30° C. for 30 minutes and then stopped by adding 100 μl 0.2 N HCl. Stimulated assay conditions involve adding 40 mM bicarbonate and 5 mM $CaCl_2$ to the above master mixture.

Cyclic AMP levels were measured in each sample using the Correlate-EIA Direct Cyclic AMP assay kit from Assay Designs as per manufacturers instructions.

In Vivo cAMP Accumulation Assay 293T cells or 4-4 cells (hsACt stably transfected into 293T) were grown in 75 cm2 Tissue Culture Flasks until nearly confluent using DMEM (10% FBS, 1% L-Glutamine, 1% Penicillin/Streptomycin). Cells were released from the flask with 3 ml of trypsin followed by addition of 7 ml of DMEM to neutralize the trypsin. Cells were mixed by pipetting up and down with 10 ml serological pipette. To a 3 ml aliquot of the cell mixture, 6 ml of DMEM (prewarmed to 37° C.) was added followed by thorough mixing by picking up the entire 9 mls using a repeat pipettor, and slowly pipetting out against the wall of container. This was repeated this ten times to ensure the mixture in homogenous. 100 μL of cells were then added to each pre-siliconized 1.7 ml Eppindorf tubes (Costar #3207) followed by a 60 min incubation at 37° C. and 5% $CO_2$. This incubation was performed in 20-tube, round, floating racks (VWR #60986-100), which enable a quick transfer of the samples to a water bath, and the ability to mix several samples simultaneously. Following the incubation, 1 μL of the compound in DMSO was added (or just DMSO for controls). The cells were mixed before and after adding the compound, by a brief (and light) vortexing. The compounds were added while the cells were in the 37° C. water bath, followed by a 10 min incubation at 37° C. and 5% $CO_2$. Following this incubation, 1 μL of IBMX or 1 μL of IBMX+Forskolin was added with Repeat Pipettor. The 4-4 cells receive the IBMX to a final concentration of 500 μM IBMX. The 293T cells receive IBMX and Forskolin to final concentration of 500 μM IBMX and 10 μM, respectively. Both the IBMX mix (for 4-4 cells), and the IBMX/FSK mix (for 293T cells) were 100×, and were dissolved in DMSO. Cells were mixed and incubated at 37° C. and 5% $CO_2$ for 15 min. The assay was stopped by placing the cells in an ice bath. Cells were pelleted by centrifugation at 2000×G for 7 min at 4° C. The supernatant was aspirated and 250 μL of 0.1 N HCl was added to each cell pellet followed by through vortexing for 1 min. Following a 10 min incubation at room temperature, 30 μL of each sample was added to 70 μL of 0.1 N HCl and the cAMP levels were measured using the protocol for the Direct Cyclic AMP Kit (Assay Designs, Inc. # 901-066). This 30 μL plus 70 μL of 0.1 N HCl makes up the sample described in step 5 of the Assay Designs' protocol. The samples should lie in the linear range of the assay.

TABLE 1

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 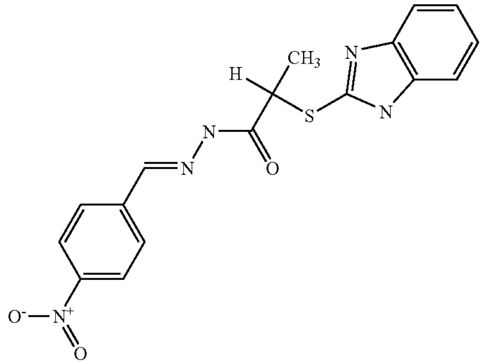 [SMILES: CC(Sc1nc2ccccc2[nH]1)C(=O)N/N=C/c1ccc([N+](=O)[O-])cc1] | KH7.101 | 10-100 | 50 | 10-100 | 50 | 30 | >120 |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 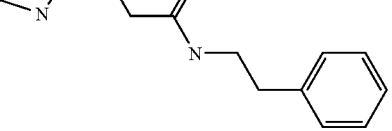 | KH7.102 | >100 | 0 | >100 | 0 | 100 | >500 |
| 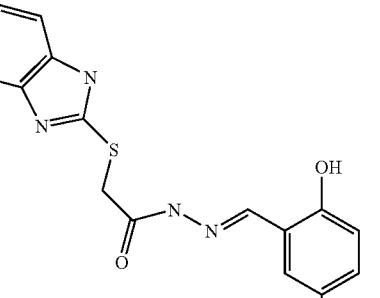 | KH7.103 | 10-100 | 100 | 10-100 | 100 | 60-120 | >120 |
| 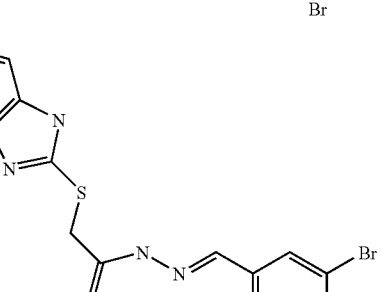 | KH7.104 | 10-100 | 85 | 10-100 | 70 | 15 | 60-120 |
| 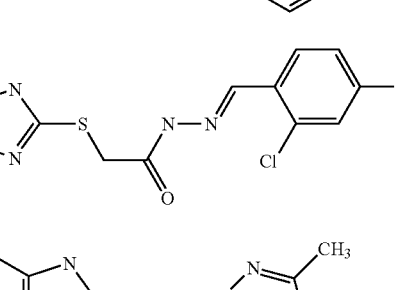 | KH7.105 | 10-100 | 90 | 10-100 | 90 | 15 | 60 |
| 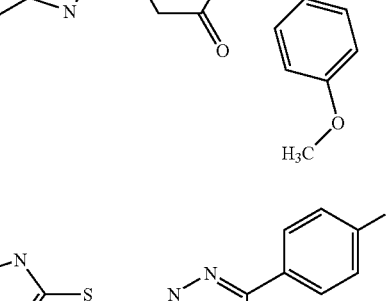 | KH7.106 | 100 | 50 | 10 | 70 | 55 | >500 |
| 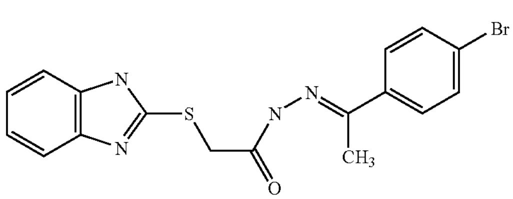 [SMILES: C/C(=N\NC(=O)CSc1nc2ccccc2[nH]1)c1ccc(Br)cc1] | KH7.107 | 10-100 | 95 | 10-100 | 95 | 60-120 | >120 |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 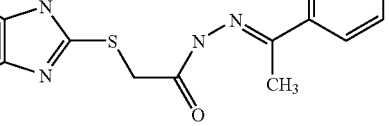 | KH7.108 | >100 | 0 | >100 | 0 | 30-60* may be cellular toxicity | 60-120* may be cellular toxicity |
| 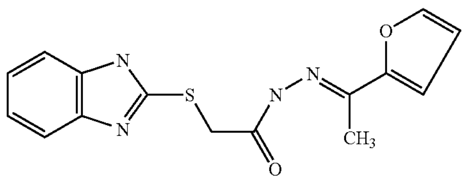 [SMILES: C/C(=N\NC(=O)CSc1nc2ccccc2[nH]1)c1ccco1] | KH7.109 | >100 | 0 | >100 | 0 | ~120 | >120 |
| 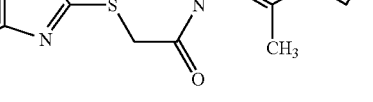 | KH7.110 | 10-100 | 90 | 10-100 | 90 | 30-60 | >120 |
| 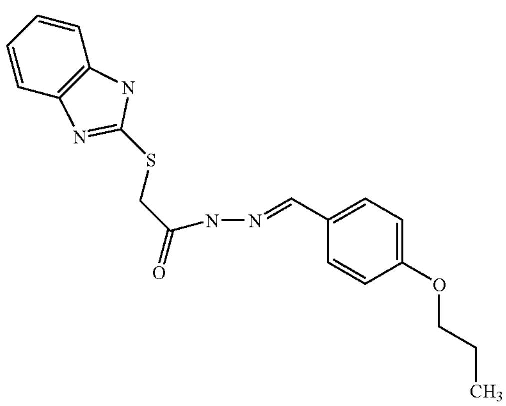 [SMILES: CCCOc1ccc(/C=N/NC(=O)CSc2nc3ccccc3[nH]2)cc1] | KH7.111 | 10-100 | 70 | 10-100 | 70 | 3-30 | 120 |
| 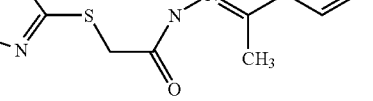 | KH7.112 | >100 | 0 | >100 | 0 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 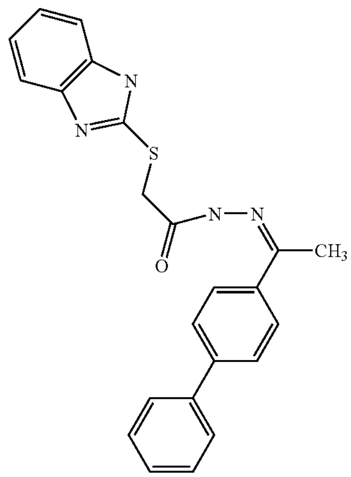 [SMILES: C/C(=N/NC(=O)CSc1nc2ccccc2[nH]1)c1ccc(-c2ccccc2)cc1] | KH7.113 | 10-100 | 80 | 10-100 | 80 | | |
| 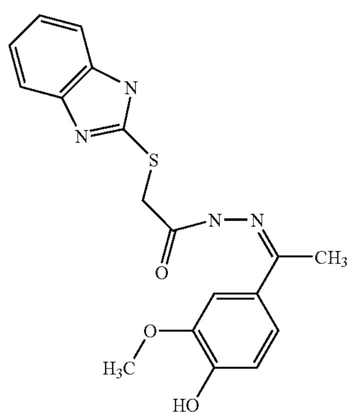 [SMILES: COc1cc(/C(C)=N\NC(=O)CSc2nc3ccccc3[nH]2)ccc1O] | KH7.114 | >100 | 0 | >100 | 0 | 56-167 | >500 |
| 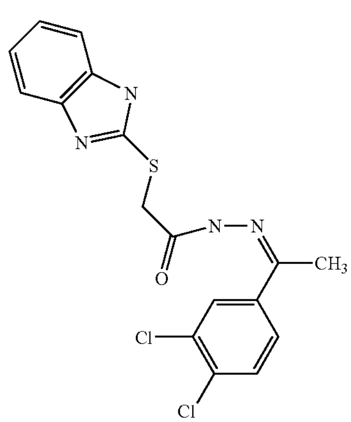 [SMILES: C/C(=N/NC(=O)CSc1nc2ccccc2[nH]1)c1ccc(Cl)c(Cl)c1] | KH7.115 | 10-100 | 80 | 10-100 | 80 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 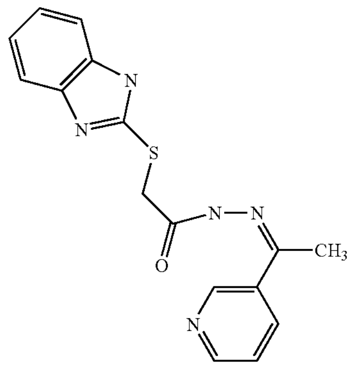 [SMILES: C/C(=N/NC(=O)CSc1nc2ccccc2[nH]1)c1cccnc1] | KH7.116 | 0.1-1 | Activation 50 | 0.1-1 | Activation 30 | | |
| 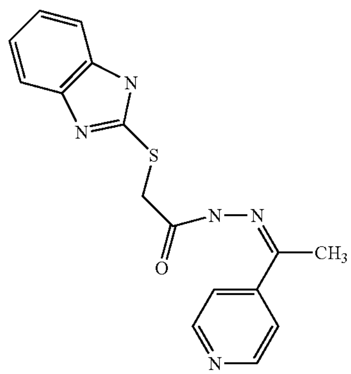 [SMILES: C/C(=N/NC(=O)CSc1nc2ccccc2[nH]1)c1ccncc1] | KH7.117 | >100 | 0 | >100 | 0 | 167-500 | >500 |
| 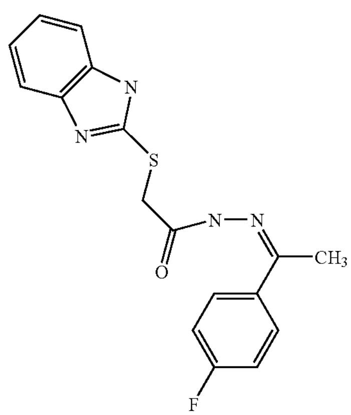 [SMILES: C/C(=N/NC(=O)CSc1nc2ccccc2[nH]1)c1ccc(F)cc1] | KH7.118 | >100 | 0 | >100 | 0 | | |
| 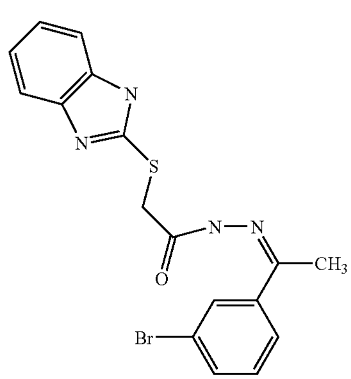 [SMILES: C/C(=N/NC(=O)CSc1nc2ccccc2[nH]1)c1cccc(Br)c1] | KH7.119 | 10-100 | 80 | 10-100 | 60 | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 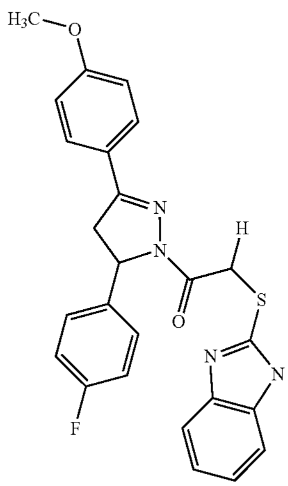 [SMILES: COc1ccc(C2=NN(C(=O)CSc3nc4ccccc4[nH]3)C(c3ccc(F)cc3)C2)cc1] | KH7.120 | 10-100 | 90 | 10-100 | 90 | | |
| 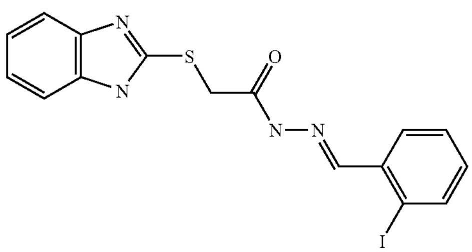 [SMILES: O=C(CSc1nc2ccccc2[nH]1)N/N=C/c1ccccc1I] | KH7.121 | 10-100 | 90 | 10-100 | 90 | | |
| 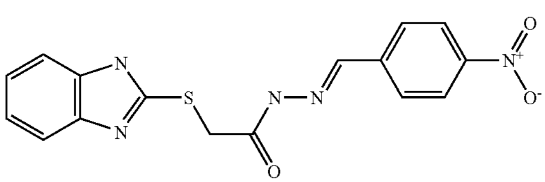 [SMILES: O=C(CSc1nc2ccccc2[nH]1)N/N=C/c1ccc([N+](=O)[O-])cc1] | KH7.122 | 100 | 50 | 100 | 50 | | |
| 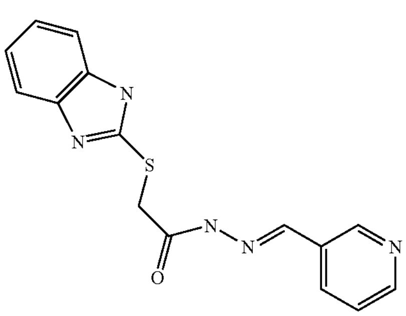 [SMILES: O=C(CSc1nc2ccccc2[nH]1)N/N=C/c1cccnc1] | KH7.123 | >100 | 0 | >100 | 0 | | |

TABLE 1-continued
| Structure | KH7 number | hsACt-Stim.[1] | % Inhibition (100 μM) hsACt-Basal[2] | % Inhibition (100 μM) | 4-4, Basal[3] | 293T + FSK[4] |
|---|---|---|---|---|---|---|
| 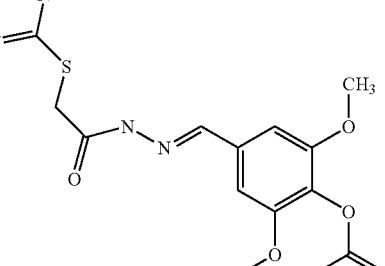 | KH7.124 | >100 | 30 | >100 | 40 | |
| 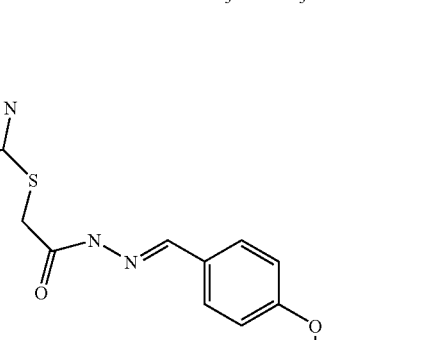 | KH7.125 | | | | | |
| 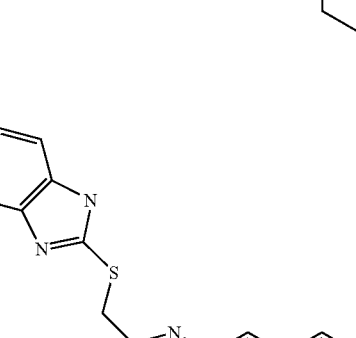 | KH7.126 | 10-100 | 50 | >100 | 40 | |
| 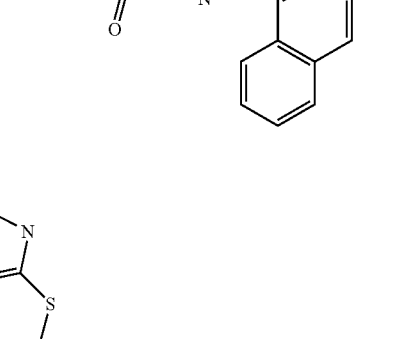 | KH7.127 | 100 | 50 | >100 | 10 | |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 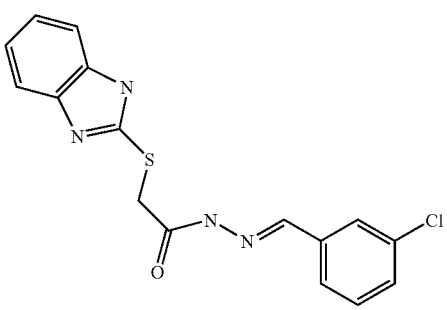 [SMILES: O=C(CSc1nc2ccccc2[nH]1)N/N=C/c1cccc(Cl)c1] | KH7.128 | 100 | 50 | 100 | 50 | | |
| 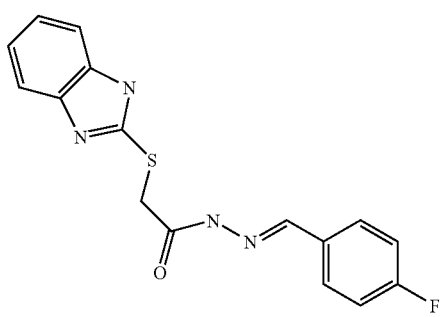 [SMILES: O=C(CSc1nc2ccccc2[nH]1)N/N=C/c1ccc(F)cc1] | KH7.129 | >100 | 0 | >100 | 0 | | |
| 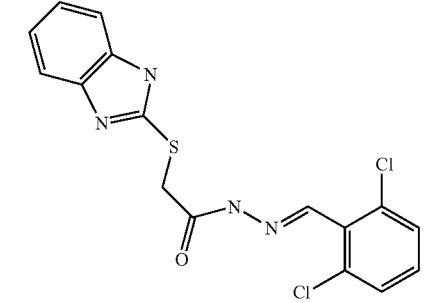 [SMILES: O=C(CSc1nc2ccccc2[nH]1)N/N=C/c1c(Cl)cccc1Cl] | KH7.130 | 100 | 50 | 100 | 50 | | |
| 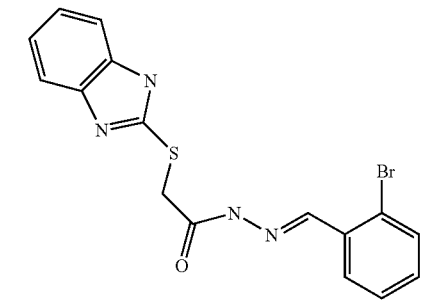 [SMILES: O=C(CSc1nc2ccccc2[nH]1)N/N=C/c1ccccc1Br] | KH7.131 | 10-100 | 60 | 10-100 | 60 | | |
| 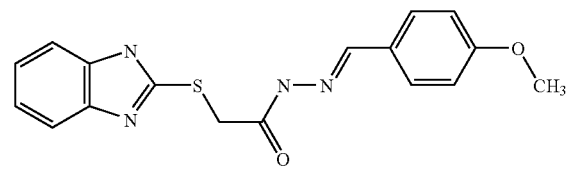 [SMILES: COc1ccc(/C=N/NC(=O)CSc2nc3ccccc3[nH]2)cc1] | KH7.132 | >100 | 0 | >100 | 10 | | |

TABLE 1-continued

| Structure | KH7 number | hsACt-Stim.[1] | % Inhibition (100 μM) hsACt-Stim.[1] | hsACt-Basal[2] | % Inhibition (100 μM) hsACt-Basal[2] | 4-4, Basal[3] | 293T + FSK[4] |
|---|---|---|---|---|---|---|---|
| 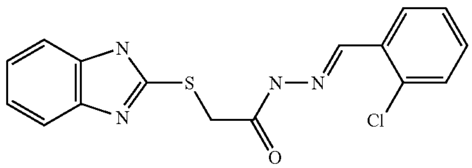 [SMILES: O=C(CSc1nc2ccccc2[nH]1)N/N=C/c1ccccc1Cl] | KH7.133 | | | 10-100 | 60 | | |
| 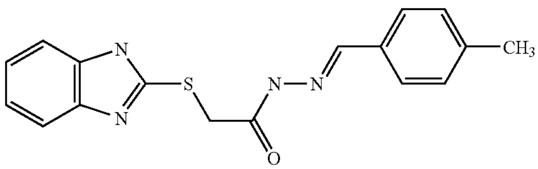 [SMILES: Cc1ccc(/C=N/NC(=O)CSc2nc3ccccc3[nH]2)cc1] | KH7.134 | >100 | 0 | >100 | 0 | | |
| 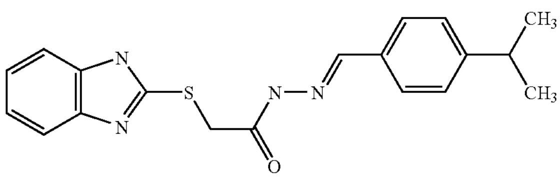 [SMILES: CC(C)c1ccc(/C=N/NC(=O)CSc2nc3ccccc3[nH]2)cc1] | KH7.135 | >100 | 0 | 100 | 50 | | |
| 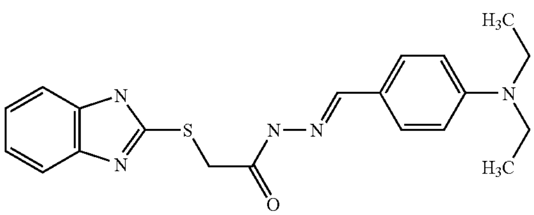 [SMILES: CCN(CC)c1ccc(/C=N/NC(=O)CSc2nc3ccccc3[nH]2)cc1] | KH7.136 | >100 | 40 | 10-100 | 80 | | |
| 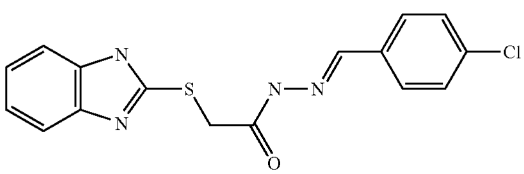 [SMILES: O=C(CSc1nc2ccccc2[nH]1)N/N=C/c1ccc(Cl)cc1] | KH7.137 | 30-100 | Activation 100 | >100 | 0 | | |
| 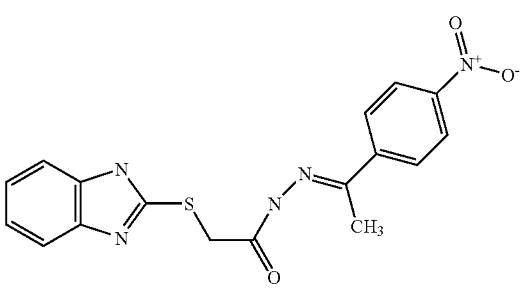 [SMILES: C/C(=N\NC(=O)CSc1nc2ccccc2[nH]1)c1ccc([N+](=O)[O-])cc1] | KH7.138 | >100 | 25 | >100 | 30 | | |
| | KH7.139 | 1.0-10 | 75 | 1.0-10 | 75 | | |
| | KH7.139 | 1.0-10 | 70 | 1.0-10 | 70 | | |

TABLE 1-continued

| Structure | KH7 number | hsACt-Stim.[1] | % Inhibition (100 μM) hsACt-Basal[2] | hsACt-Basal[2] | % Inhibition (100 μM) 4-4, Basal[3] | 293T + FSK[4] |
|---|---|---|---|---|---|---|
| 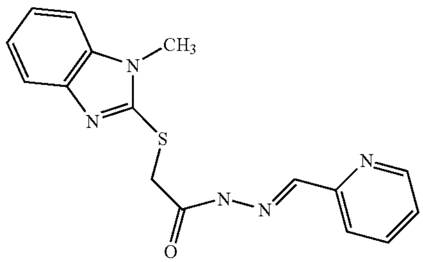 [SMILES: Cn1c(SCC(=O)N/N=C/c2ccccn2)nc2ccccc21] | KH7.140 | >100 | 0 | >100 | 0 | |
| 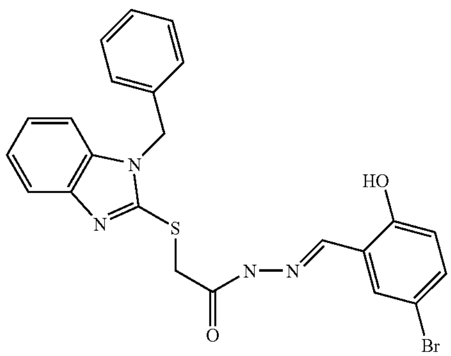 [SMILES: O=C(CSc1nc2ccccc2n1Cc1ccccc1)N/N=C/c1cc(Br)ccc1O] | KH7.141 | 1 | 80 | 1.0-10 | 80 | |
| 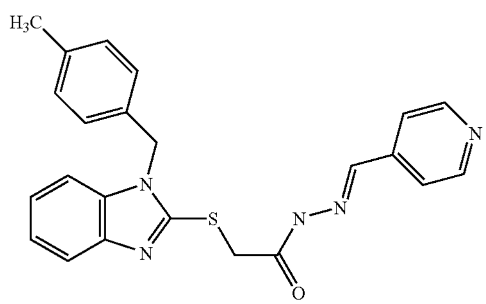 [SMILES: Cc1ccc(Cn2c(SCC(=O)N/N=C/c3ccncc3)nc3ccccc32)cc1] | KH7.142 | 1.0-10 | Activation @ 100 | >100 | 0 | |
| 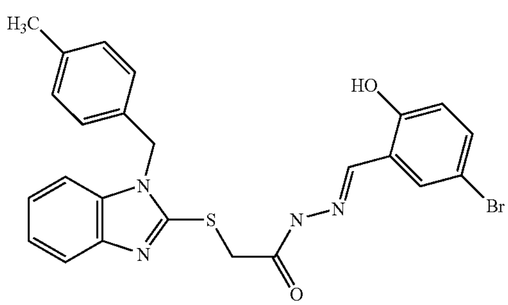 [SMILES: Cc1ccc(Cn2c(SCC(=O)N/N=C/c3cc(Br)ccc3O)nc3ccccc32)cc1] | KH7.143 | 1 | 75 | 1 | 75 | |
| 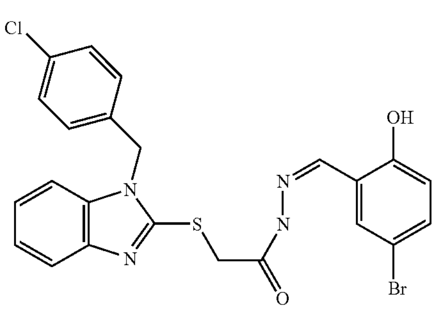 [SMILES: O=C(CSc1nc2ccccc2n1Cc1ccc(Cl)cc1)N/N=C\c1cc(Br)ccc1O] | KH7.144 | 1 | 80 | 1 | 70 | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 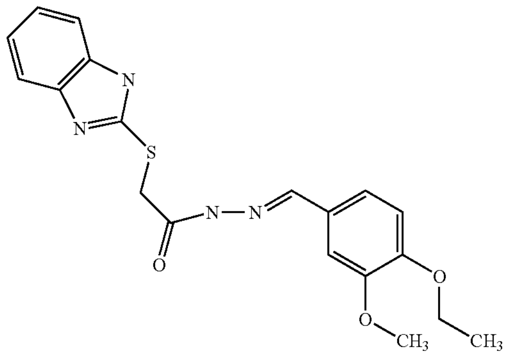 [SMILES: CCOc1ccc(/C=N/NC(=O)CSc2nc3ccccc3[nH]2)cc1OC] | KH7.145 | >100 | 20 | >100 | 0 | | |
| 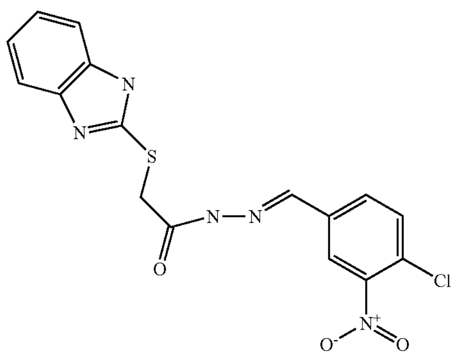 [SMILES: O=C(CSc1nc2ccccc2[nH]1)N/N=C/c1ccc(Cl)c([N+](=O)[O-])c1] | KH7.146 | >100 | 40 | 100 | 50 | | |
| 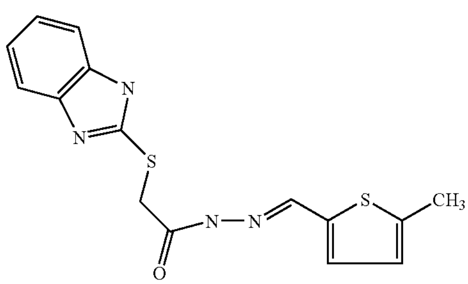 [SMILES: Cc1ccc(/C=N/NC(=O)CSc2nc3ccccc3[nH]2)s1] | KH7.147 | 10 | 60 | 10-100 | 60 | | |
| 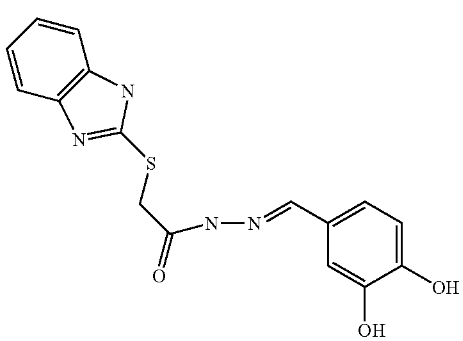 [SMILES: O=C(CSc1nc2ccccc2[nH]1)N/N=C/c1ccc(O)c(O)c1] | KH7.148 | 1.0-10 | 80 | 10-100 | 70 | | |

TABLE 1-continued
| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 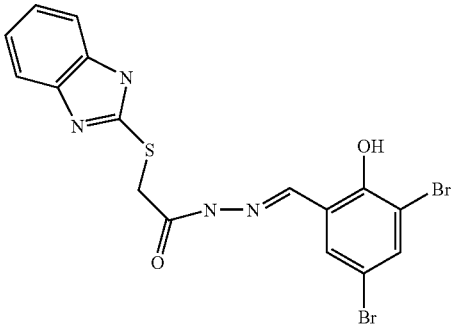 [SMILES: O=C(CSc1nc2ccccc2[nH]1)N/N=C/c1cc(Br)cc(Br)c1O] | KH7.149 | 1 | 85 | 1 | 90 | | |
| 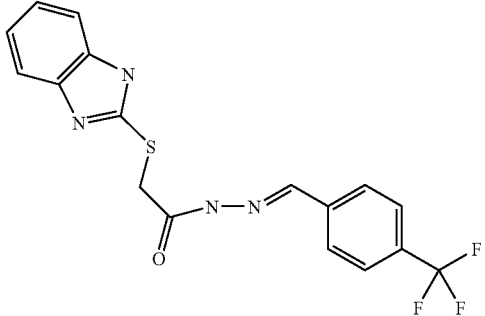 [SMILES: O=C(CSc1nc2ccccc2[nH]1)N/N=C/c1ccc(C(F)(F)F)cc1] | KH7.150 | >100 | 0 | >100 | 0 | | |
| 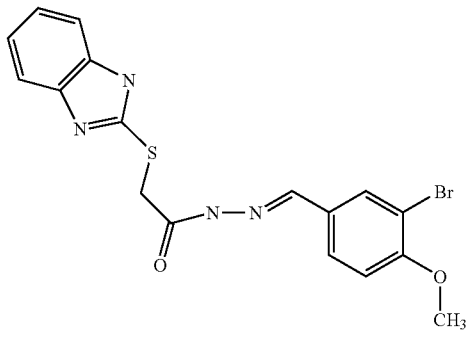 [SMILES: COc1ccc(/C=N/NC(=O)CSc2nc3ccccc3[nH]2)cc1Br] | KH7.151 | 10-100 | 50 | 10-100 | 75 | | |
| 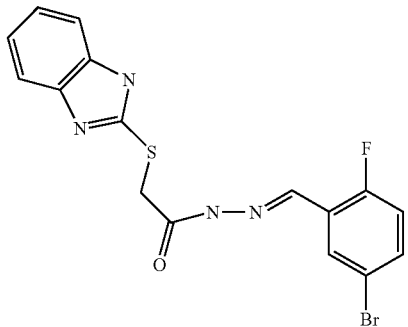 [SMILES: O=C(CSc1nc2ccccc2[nH]1)N/N=C/c1cc(Br)ccc1F] | KH7.152 | | | 10-100 | 60 | | |

TABLE 1-continued
| Structure | KH7 number | hsACt-Stim.[1] | % Inhibition (100 μM) hsACt-Stim.[1] | hsACt-Basal[2] | % Inhibition (100 μM) hsACt-Basal[2] | 4-4, Basal[3] | 293T + FSK[4] |
|---|---|---|---|---|---|---|---|
| 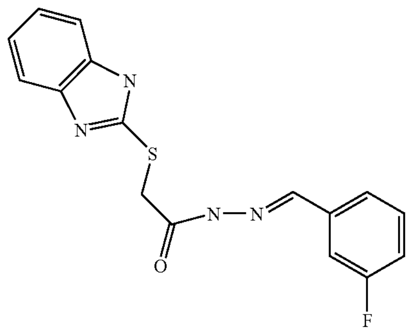 [SMILES: O=C(CSc1nc2ccccc2[nH]1)N/N=C/c1cccc(F)c1] | KH7.153 | >100 | 0 | >100 | 0 | | |
| 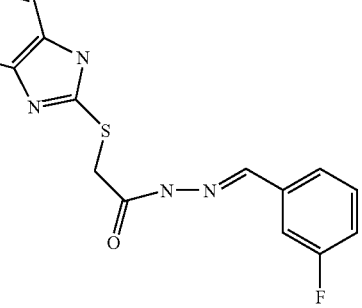 | | | | | | | |
| 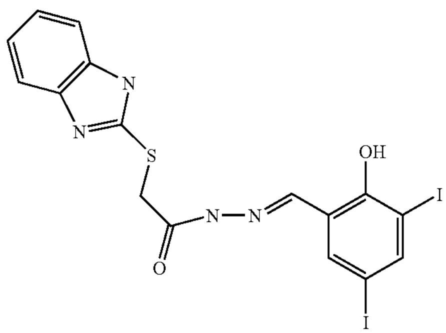 [SMILES: O=C(CSc1nc2ccccc2[nH]1)N/N=C/c1cc(I)cc(I)c1O] | KH7.154 | 0.1-1 | 85 | 0.1-1 | 100 | | |
| 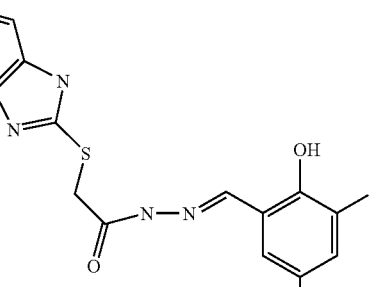 | | | | | | | |
| 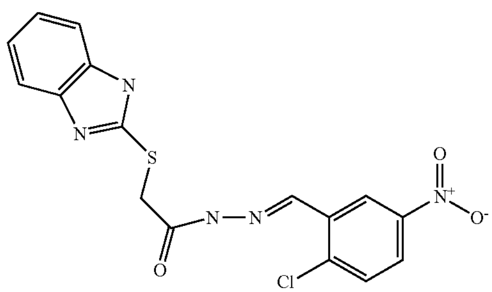 [SMILES: O=C(CSc1nc2ccccc2[nH]1)N/N=C/c1cc([N+](=O)[O-])ccc1Cl] | KH7.155 | >100 | 0 | >100 | 0 | | |
| 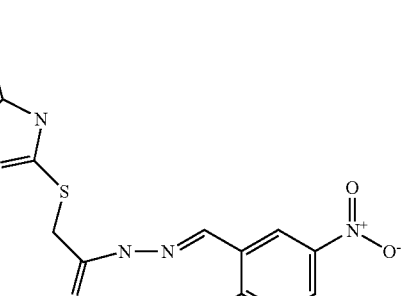 | | | | | | | |
| 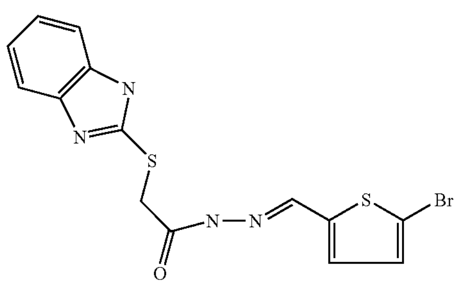 [SMILES: O=C(CSc1nc2ccccc2[nH]1)N/N=C/c1ccc(Br)s1] | KH7.156 | | | | | | |
| 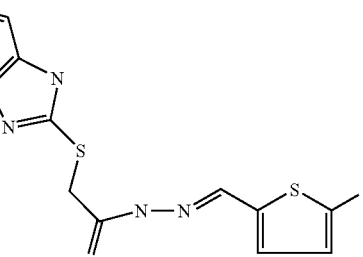 | | | | | | | |

TABLE 1-continued

| Structure | KH7 number | hsACt-Stim.[1] | % Inhibition (100 μM) | hsACt-Basal[2] | % Inhibition (100 μM) | 4-4, Basal[3] | 293T + FSK[4] |
|---|---|---|---|---|---|---|---|
| 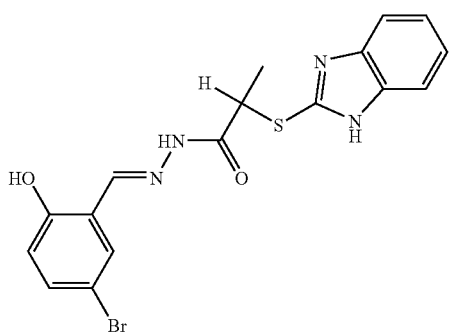 | KH7.157 | | | | | | |

[1] "hsACt-Stim." is the approximate IC50 (or the dose range where the IC50 should lie) that inhibited the activity of human sAC in vitro - in this case, the stimulated activity of human sAC (i.e., calcium and bicarbonate stimulated). "% inhibition (100 μM)" is the percent that activity (the stimulated human sAC in vitro activity) was inhibited by 100 μM of compound.
[2] "hsACt-Basal" is the approximate IC50 (or the dose range where the IC50 should lie) that inhibited the activity of human sAC in vitro - in this case, the basal activity of human sAC (i.e., just Mg-ATP as substrate, with no calcium or bicarbonate added). "% inhibition (100 μM)" is the percent that activity (the basal human sAC in vitro activity) was inhibited by 100 μM of compound.
[3] "4-4, Basal" is activity in a cellular assay - it is the approximate IC50 (or the dose range where the IC50 should lie) that inhibited the activity of a stable cell line overexpressing human sAC - basically, this is a good indication of in vivo efficacy against human sAC
[4] 293T + FSK is also a celllular assay, but in this case, the activity that is being measured is due to endogenous transmembrane adenylyl cyclases. This is an indication of the selectivity of these compounds versus the other forms of adenylyl cyclase in humans.

Example 2

Effects of KH7 Compounds on *Trypanosoma brucei*

*T. brucei* has multiple adenylyl cyclase genes. The vast majority have similar topology: a large variable extracellular region, a single transmembrane region, and a highly conserved catalytic domain. The catalytic domain is Class IIId and is homologous to fungal adenylyl cyclases. We therefore sought to determine the effect of KH7, KH7.15, and KH7.14 on *T. brucei* growth and lysate activity. The structures of KH7, KH7.14, and KH7.15 are

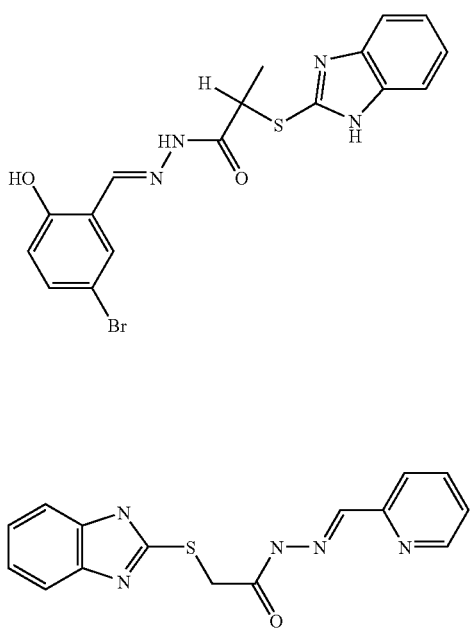

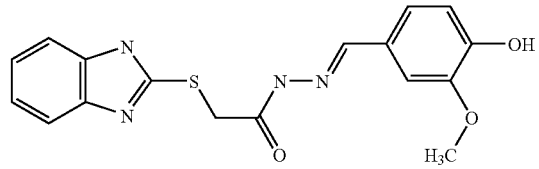

Bloodstream form and procyclic form cells were grown in the presence of increasing concentrations of KH7, KH7.15, KH7.14 in the range of 1 μM to 300 μM. Compounds were dissolved in DMSO and added directly to growth media (HMI-9 for Bloodstream form cells; SDM-79 for procyclic form cells) at a final DMSO concentration of 1%. Cell density was monitored using a Coulter Counter. In Bloodstream forms, KH7 was effective at preventing growth at concentrations between 3 to 10 μM (see FIG. 1), while KH7.15 and KH7.14 prevented growth only at concentrations in excess of 100 μM, presumably via non-specific toxicity. None of the tested compounds had any effect on growth of procyclic forms.

Figure 2:
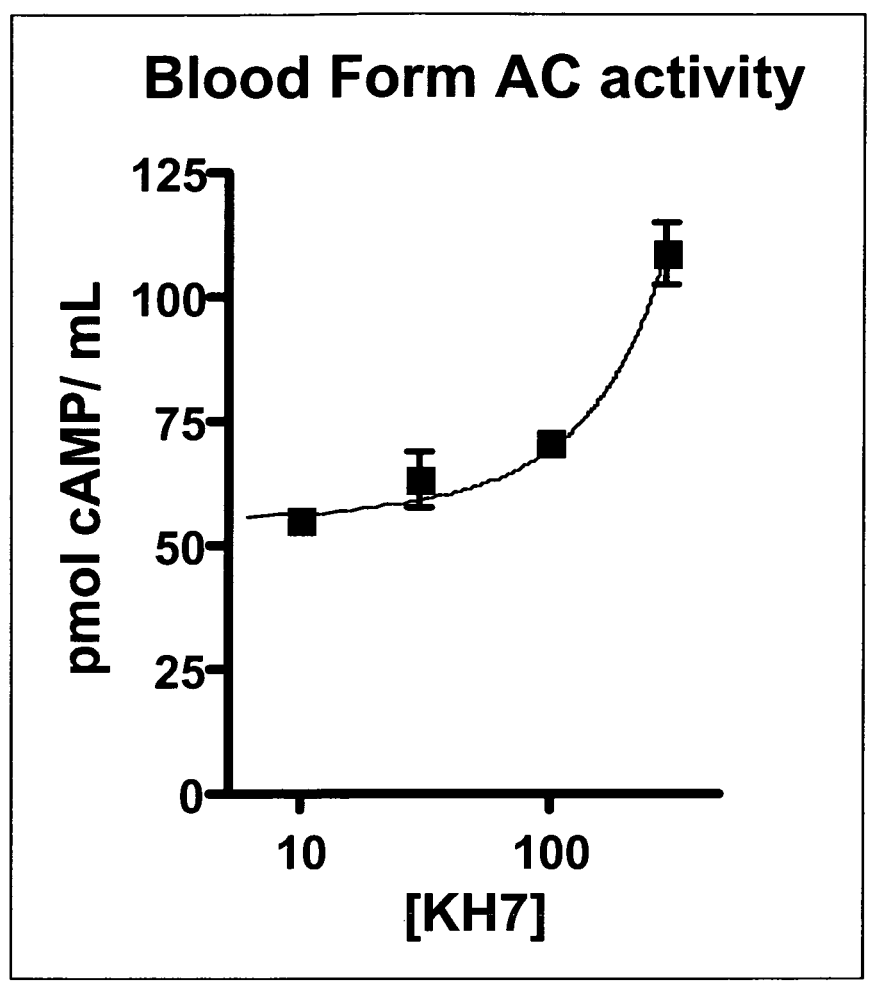
FIG. 2. The effect of the KH7 compound on adenylyl cyclase activity from *Trypansoma brucei* cell lysates. Adenyly cyclase activity is measured by the amount of cAMP generated, which is plotted as pmol cAMP/mL against the μM concentrations of KH7.

The effect of these compounds on lysate activity was tested using whole cell lysate of the bloodstream form. Briefly, $5 \times 10^6$ cells were sonicated (on ice) in a lysis buffer consisting of 2 mM Tris-HCl, 15 mM KCl, 1 mM EDTA, 1 mM 2-mercaptoethanol, 100 μM PMSF, and 1 μg/mL aprotinin/leupeptin. Adenylyl cyclase assays were conducted using 20 μL of lysate/assay in the presence of 15 mM $MgCl_2$ and 1 mM ATP in 50 mM Tris-HCl at pH=7.5 at 30° C. KH7.14 and KH7.15 had no effect on activity at any concentration while 100 μM KH7 stimulated AC activity in the whole cell lysate between 1.5-2 fold (see FIG. 2). The observation that KH7 prevents growth of bloodstream form cells in vitro via activation of adenylyl cyclase is consistent with the idea that the cAMP pathway controls the cell cycle.

We claim:
1. A method for the treatment of a subject with an infection by a Eukaryotic pathogen, the method comprising:

administering to the subject a therapeutic amount of an inhibitor of an adenylyl cyclase of the Eukaryotic pathogen, wherein the inhibitor of adenylyl cyclase is selected from the group consisting of:

KH7.102

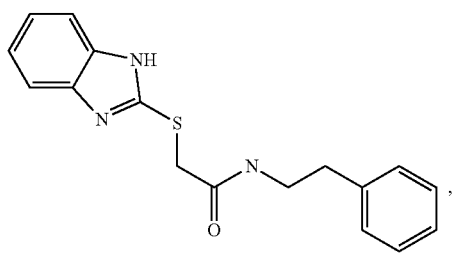

KH7.109

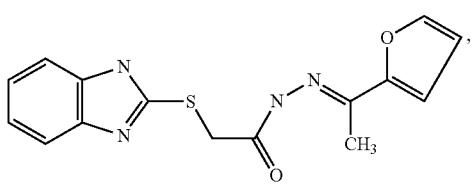

KH7.112

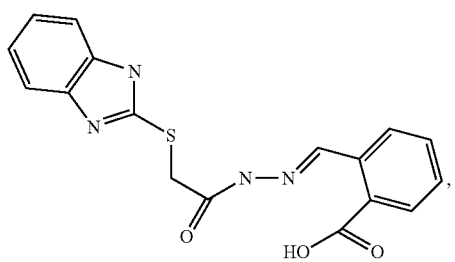

KH7.114

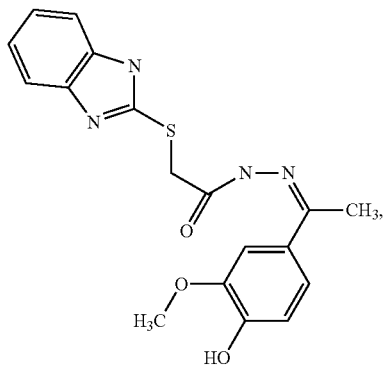

KH7.117

KH7.118

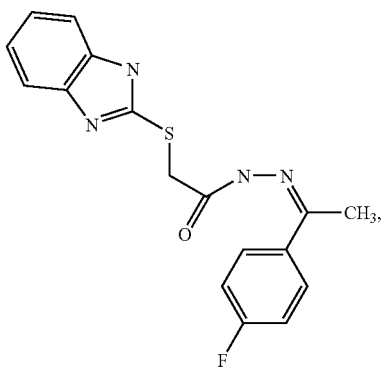

KH7.150

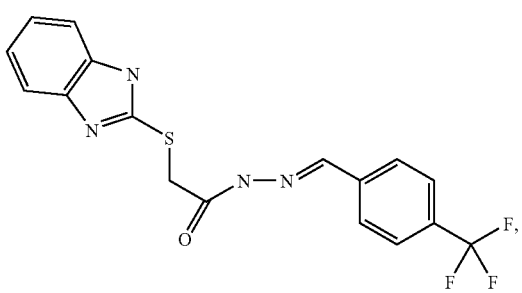

and combinations thereof.

2. The method of claim 1, wherein the amount of inhibitor of the pathogen's adenylyl cyclase administered is effective at substantially preventing the pathogen from changing to a pathogenic state from a non-pathogenic state,
or wherein the amount of inhibitor of the pathogen's adenylyl cyclase administered is effective to cause the pathogen to substantially revert to a non-pathogenic state from a pathogenic state.

3. The method of claim 2, wherein the inhibitor of the pathogen's adenylyl cyclase substantially prevents the infecting pathogen from increasing growth rate.

4. The method of claim 2, wherein the inhibitor of the pathogen's adenylyl cyclase reduces or substantially prevents the expression of one or more virulence factors.

5. The method of claim 1, wherein the inhibitor of the pathogen's adenylyl cyclase has a substantially biocidal effect on the infecting pathogen.

6. The method of claim 1, wherein the amount of inhibitor of adenylyl cyclase administered does not substantially kill the pathogen.

7. The method of claim 1, wherein the adenylyl cyclase is $CO_2/HCO_3^-/pH$ sensitive.

8. The method of claim 7, wherein the inhibitor affects the response of the infecting pathogen adenylyl cyclase to $CO_2$.

9. The method of claim 7, wherein the inhibitor affects the response of the infecting pathogen adenylyl cyclase to $HCO_3^-$.

10. The method of claim 7, wherein the inhibitor affects the response of the infecting pathogen adenylyl cyclase to pH.

11. The method of claim 1, wherein the pathogen's adenylyl cyclase is a Class III adenylyl cyclase.

12. The method of claim 1, wherein the infection is caused by a pathogen that is resistant to one or more anti-microbial agents.

13. The method of claim 1, wherein the subject is a plant.

14. The method of claim 1, wherein the subject is an animal.

15. The method of claim 1, wherein the subject is a bird.

16. The method of claim 15, wherein the bird is poultry.

17. The method of claim 1, wherein the subject is a fish.

18. The method of claim 1, wherein the subject is a mammal.

19. The method of claim 18, wherein the mammal is livestock or pet.

20. The method of claim 19 wherein the livestock animal is selected form the group consisting of cattle, swine, sheep, and horses.

21. The method of claim 19 wherein the pet is selected form the group consisting of dogs and cats.

22. The method of claim 18, wherein the mammal is a human.

23. The method of claim 1, wherein the inhibitor of the pathogen's adenylyl cyclase does not inhibit adenylyl cyclases of the subject.

24. The method of claim 1, wherein the inhibitor of the pathogen's adenylyl cyclase is selective relative to adenylyl cyclases of the subject.

25. The method of claim 1, wherein the inhibitor of the pathogen's adenylyl cyclase is sufficiently selective against adenylyl cyclases of the subject that a therapeutic effect upon the infecting pathogen can be achieved without toxic regulation of subject's adenylyl cyclase occurring.

26. The method of claim 1, further comprising administration of one or more additional therapeutic agents.

27. The method of claim 26, wherein the additional therapeutic agent is an anti-microbial agent.

* * * * *